(12) United States Patent
Amirana et al.

(10) Patent No.: US 12,076,081 B2
(45) Date of Patent: Sep. 3, 2024

(54) SYSTEMS AND METHODS FOR OPTICAL INTERROGATION OF ABLATION LESIONS

(71) Applicant: 460Medical, Inc., Weston, MA (US)

(72) Inventors: Omar Amirana, Weston, MA (US); Terrance J. Ransbury, Chapel Hill, NC (US); Arun Jaganathan, Boston, MA (US)

(73) Assignee: 460Medical, Inc., Weston, MA (US)

( * ) Notice: Subject to any disclaimer, the term of this patent is extended or adjusted under 35 U.S.C. 154(b) by 390 days.

(21) Appl. No.: 17/145,188

(22) Filed: Jan. 8, 2021

(65) Prior Publication Data
US 2021/0205017 A1    Jul. 8, 2021

Related U.S. Application Data

(60) Provisional application No. 62/958,419, filed on Jan. 8, 2020.

(51) Int. Cl.
*A61B 18/24* (2006.01)
*A61B 17/32* (2006.01)
(Continued)

(52) U.S. Cl.
CPC ...... *A61B 18/24* (2013.01); *A61B 17/320068* (2013.01); *A61B 18/02* (2013.01);
(Continued)

(58) Field of Classification Search
CPC . A61B 18/24; A61B 17/320068; A61B 18/02; A61B 18/08; A61B 18/1492;
(Continued)

(56) References Cited

U.S. PATENT DOCUMENTS 3,387,305 A    6/1968    Shafer
3,831,467 A    8/1974    Moore
(Continued)

FOREIGN PATENT DOCUMENTS

CN    1289239    3/2001
CN    1764419    4/2006
(Continued)

OTHER PUBLICATIONS

Anderson et al. "Real-time spectroscopic assessment of thermal damage: implications for radiofrequency ablation". J Gastrointest Surg. 2004; 8: 660-669.
(Continued)

*Primary Examiner* — Linda C Dvorak
*Assistant Examiner* — Abigail Bock
(74) *Attorney, Agent, or Firm* — Greenberg Traurig, LLP; David J. Dykeman; Roman Fayerberg

(57) ABSTRACT

In some embodiments, a system for optical tissue interrogation comprises a catheter having a plurality of electrodes disposed in an array at a distal end of the catheter, the plurality of electrodes being configured to deliver ablation energy to tissue; and one or more optical fibers extending through the catheter to deliver light from a light source to the tissue and to deliver optical information comprising nicotinamide adenine dinucleotide hydrogen (NADH) fluorescence from the tissue to a sensor, wherein each electrode of the plurality of electrodes is associated with at least one of the one or more optical fibers.

22 Claims, 24 Drawing Sheets

(51) Int. Cl.
  *A61B 18/00* (2006.01)
  *A61B 18/02* (2006.01)
  *A61B 18/08* (2006.01)
  *A61B 18/14* (2006.01)
  *A61B 18/18* (2006.01)
  *A61B 34/20* (2016.01)
  *A61N 1/32* (2006.01)

(52) U.S. Cl.
  CPC .......... *A61B 18/08* (2013.01); *A61B 18/1492* (2013.01); *A61B 18/1815* (2013.01); *A61N 1/327* (2013.01); *A61B 2017/320069* (2017.08); *A61B 2018/00375* (2013.01); *A61B 2018/00577* (2013.01); *A61B 2018/0212* (2013.01); *A61B 2018/1467* (2013.01); *A61B 2018/1861* (2013.01); *A61B 34/20* (2016.02); *A61B 2218/002* (2013.01)

(58) Field of Classification Search
  CPC .... A61B 18/1815; A61B 2017/320069; A61B 2018/00577; A61B 2018/0212; A61B 2018/1467; A61B 2018/1861; A61N 1/327
  See application file for complete search history.

(56) References Cited

U.S. PATENT DOCUMENTS

| | | | |
|---|---|---|---|
| 4,024,873 | A | 5/1977 | Antoshkiw et al. |
| 4,619,247 | A | 10/1986 | Inoue et al. |
| 5,074,306 | A | 12/1991 | Green et al. |
| 5,187,572 | A | 2/1993 | Nakamura et al. |
| 5,350,375 | A | 9/1994 | Deckelbaum et al. |
| 5,419,323 | A | 5/1995 | Kittrell et al. |
| 5,421,337 | A | 6/1995 | Richards-Kortum et al. |
| 5,507,287 | A | 4/1996 | Palcic et al. |
| 5,540,681 | A | 7/1996 | Strul et al. |
| 5,584,799 | A | 12/1996 | Gray |
| 5,590,660 | A | 1/1997 | MacAulay et al. |
| 5,657,760 | A | 8/1997 | Ying et al. |
| 5,713,364 | A | 2/1998 | DeBaryshe et al. |
| 5,749,830 | A | 5/1998 | Kaneko et al. |
| 5,833,688 | A | 11/1998 | Sieben et al. |
| 5,885,258 | A | 3/1999 | Sachdeva et al. |
| 5,904,651 | A | 5/1999 | Swanson et al. |
| 5,954,665 | A | 9/1999 | Haim |
| 6,064,069 | A | 5/2000 | Nakano et al. |
| 6,112,123 | A | 8/2000 | Kelleher et al. |
| 6,124,597 | A | 9/2000 | Shehada et al. |
| 6,174,291 | B1 | 1/2001 | McMahon et al. |
| 6,178,346 | B1 | 1/2001 | Amundson et al. |
| 6,197,021 | B1 | 3/2001 | Panescu et al. |
| 6,208,886 | B1 | 3/2001 | Alfano et al. |
| 6,217,573 | B1 | 4/2001 | Webster et al. |
| 6,219,566 | B1 | 4/2001 | Weersink et al. |
| 6,251,107 | B1 | 6/2001 | Schaer |
| 6,289,236 | B1 | 9/2001 | Koenig et al. |
| 6,309,352 | B1 | 10/2001 | Oraevsky et al. |
| 6,343,228 | B1 | 1/2002 | Qu |
| 6,423,055 | B1 | 7/2002 | Farr et al. |
| 6,423,057 | B1 | 7/2002 | He et al. |
| 6,450,971 | B1 | 9/2002 | Andrus et al. |
| 6,485,413 | B1 | 11/2002 | Boppart et al. |
| 6,516,217 | B1 | 2/2003 | Tsujita |
| 6,522,913 | B2 | 2/2003 | Swanson et al. |
| 6,542,767 | B1 | 4/2003 | McNichols et al. |
| 6,572,609 | B1 | 6/2003 | Farr et al. |
| 6,584,360 | B2 | 6/2003 | Francischelli et al. |
| 6,626,900 | B1 | 9/2003 | Sinofsky et al. |
| 6,648,883 | B2 | 11/2003 | Francischelli et al. |
| 6,658,279 | B2 | 12/2003 | Swanson et al. |
| 6,663,622 | B1 | 12/2003 | Foley et al. |
| 6,663,627 | B2 | 12/2003 | Francischelli et al. |
| 6,671,535 | B1 | 12/2003 | McNichols et al. |
| 6,697,657 | B1 | 2/2004 | Shehada et al. |
| 6,706,038 | B2 | 3/2004 | Francischelli et al. |
| 6,716,196 | B2 | 4/2004 | Lesh et al. |
| 6,743,225 | B2 | 6/2004 | Sanchez et al. |
| 6,746,401 | B2 | 6/2004 | Panescu |
| 6,761,716 | B2 | 7/2004 | Kadhiresan et al. |
| 6,825,928 | B2 | 11/2004 | Liu et al. |
| 6,936,047 | B2 | 8/2005 | Nasab et al. |
| 6,937,885 | B1 | 8/2005 | Lewis et al. |
| 6,942,657 | B2 | 9/2005 | Sinofsky et al. |
| 6,953,457 | B2 | 10/2005 | Farr et al. |
| 6,974,454 | B2 | 12/2005 | Hooven |
| 6,975,898 | B2 | 12/2005 | Seibel |
| 6,975,899 | B2 | 12/2005 | Faupel et al. |
| 6,979,290 | B2 | 12/2005 | Mourlas et al. |
| 6,989,010 | B2 | 1/2006 | Francischelli et al. |
| 7,001,383 | B2 | 2/2006 | Keidar |
| 7,029,470 | B2 | 4/2006 | Francischelli et al. |
| 7,047,068 | B2 | 5/2006 | Haissaguerre |
| 7,130,672 | B2 | 10/2006 | Pewzner et al. |
| 7,192,427 | B2 | 3/2007 | Chapelon et al. |
| 7,207,984 | B2 | 4/2007 | Farr et al. |
| 7,232,437 | B2 | 6/2007 | Berman et al. |
| 7,235,045 | B2 | 6/2007 | Wang et al. |
| 7,250,048 | B2 | 7/2007 | Francischelli et al. |
| 7,252,664 | B2 | 8/2007 | Nasab et al. |
| 7,255,695 | B2 | 8/2007 | Falwell et al. |
| 7,289,205 | B2 | 10/2007 | Yaroslavsky et al. |
| 7,306,593 | B2 | 12/2007 | Keidar et al. |
| 7,338,485 | B2 | 3/2008 | Brucker et al. |
| 7,357,796 | B2 | 4/2008 | Farr et al. |
| 7,367,944 | B2 | 5/2008 | Rosemberg et al. |
| 7,367,972 | B2 | 5/2008 | Francischelli et al. |
| 7,417,740 | B2 | 8/2008 | Alphonse et al. |
| 7,497,858 | B2 | 3/2009 | Chapelon et al. |
| 7,527,625 | B2 | 5/2009 | Knight et al. |
| 7,534,204 | B2 | 5/2009 | Starksen et al. |
| 7,539,530 | B2 | 5/2009 | Caplan et al. |
| 7,587,236 | B2 | 9/2009 | Demos et al. |
| 7,591,816 | B2 | 9/2009 | Wang et al. |
| 7,596,404 | B2 | 9/2009 | Maier et al. |
| 7,598,088 | B2 | 10/2009 | Balas |
| 7,640,046 | B2 | 12/2009 | Pastore |
| 7,662,152 | B2 | 2/2010 | Sharareh et al. |
| 7,681,579 | B2 | 3/2010 | Schwartz |
| 7,727,229 | B2 | 6/2010 | He et al. |
| 7,727,231 | B2 | 6/2010 | Swanson |
| 7,729,750 | B2 | 6/2010 | Tromberg et al. |
| 7,766,907 | B2 | 8/2010 | Dando et al. |
| 7,776,033 | B2 | 8/2010 | Swanson |
| 7,822,460 | B2 | 10/2010 | Halperin et al. |
| 7,824,397 | B2 | 11/2010 | McAuley |
| 7,824,399 | B2 | 11/2010 | Francischelli et al. |
| 7,837,676 | B2 | 11/2010 | Sinelnikov et al. |
| 7,846,157 | B2 | 12/2010 | Kozel |
| 7,862,561 | B2 | 1/2011 | Swanson et al. |
| 7,877,128 | B2 | 1/2011 | Schwartz |
| 7,918,850 | B2 | 4/2011 | Govari et al. |
| 7,930,016 | B1 | 4/2011 | Saadat |
| 7,942,871 | B2 | 5/2011 | Thapliyal et al. |
| 7,950,397 | B2 | 5/2011 | Thapliyal et al. |
| 7,974,683 | B2 | 7/2011 | Balaset et al. |
| 7,976,537 | B2 | 7/2011 | Lieber et al. |
| 7,979,107 | B2 | 7/2011 | Lin et al. |
| 7,992,573 | B2 | 8/2011 | Wilson et al. |
| 7,996,078 | B2 | 8/2011 | Paul et al. |
| 8,007,433 | B2 | 8/2011 | Iketani |
| 8,024,027 | B2 | 9/2011 | Freeman et al. |
| 8,025,661 | B2 | 9/2011 | Arnold et al. |
| 8,050,746 | B2 | 11/2011 | Saadat et al. |
| 8,078,266 | B2 | 12/2011 | Saadat et al. |
| 8,123,742 | B2 | 2/2012 | Berger |
| 8,123,745 | B2 | 2/2012 | Beeckler et al. |
| 8,129,105 | B2 | 3/2012 | Zuckerman |
| 8,131,350 | B2 | 3/2012 | Saadat et al. |
| 8,137,333 | B2 | 3/2012 | Saadat et al. |
| 8,144,966 | B2 | 3/2012 | Provenzano et al. |
| 8,146,603 | B2 | 4/2012 | Thapliyal et al. |
| 8,147,484 | B2 | 4/2012 | Lieber et al. |

(56) References Cited

U.S. PATENT DOCUMENTS

| | | |
|---|---|---|
| 8,152,795 B2 | 4/2012 | Farr et al. |
| 8,160,680 B2 | 4/2012 | Boyden et al. |
| 8,175,688 B2 | 5/2012 | Lewis et al. |
| 8,180,436 B2 | 5/2012 | Boyden et al. |
| 8,188,446 B2 | 5/2012 | Ohno |
| 8,195,271 B2 | 6/2012 | Rahn |
| 8,203,709 B2 | 6/2012 | Ishii |
| 8,219,183 B2 | 7/2012 | Mashke et al. |
| 8,221,310 B2 | 7/2012 | Saadat et al. |
| 8,235,985 B2 | 8/2012 | Saadat et al. |
| 8,241,272 B2 | 8/2012 | Arnold et al. |
| 8,267,926 B2 | 9/2012 | Paul et al. |
| 8,277,444 B2 | 10/2012 | Arnold et al. |
| 8,298,227 B2 | 10/2012 | Leo et al. |
| 8,309,346 B2 | 11/2012 | Zuckerman |
| 8,317,783 B2 | 11/2012 | Cao et al. |
| 8,333,012 B2 | 12/2012 | Rothe et al. |
| 8,353,907 B2 | 1/2013 | Winkler et al. |
| 8,357,149 B2 | 1/2013 | Govari et al. |
| 8,366,705 B2 | 2/2013 | Arnold et al. |
| 8,369,922 B2 | 2/2013 | Paul et al. |
| 8,374,682 B2 | 2/2013 | Freeman et al. |
| 8,382,750 B2 | 2/2013 | Brannan |
| 8,403,925 B2 | 3/2013 | Miller et al. |
| 8,414,508 B2 | 4/2013 | Thapliyal et al. |
| 8,417,321 B2 | 4/2013 | Saadat et al. |
| 8,417,323 B2 | 4/2013 | Uzunbajakava et al. |
| 8,419,613 B2 | 4/2013 | Saadat et al. |
| 8,435,232 B2 | 5/2013 | Aeby et al. |
| 8,444,639 B2 | 5/2013 | Arnold et al. |
| 8,460,285 B2 | 6/2013 | Wang et al. |
| 8,463,366 B2 | 6/2013 | Freeman et al. |
| 8,500,730 B2 | 8/2013 | Lee et al. |
| 8,504,132 B2 | 8/2013 | Friedman et al. |
| 8,511,317 B2 | 8/2013 | Thapliyal et al. |
| 8,540,704 B2 | 9/2013 | Melsky et al. |
| 8,548,567 B2 | 10/2013 | Maschke et al. |
| 8,556,892 B2 | 10/2013 | Hong et al. |
| 8,583,220 B2 | 11/2013 | Schwartz |
| 8,603,084 B2 | 12/2013 | Fish et al. |
| 8,607,800 B2 | 12/2013 | Thapliyal et al. |
| 8,628,520 B2 | 1/2014 | Sharareh et al. |
| 8,641,705 B2 | 2/2014 | Leo et al. |
| 8,641,706 B2 | 2/2014 | Lieber et al. |
| 8,690,758 B2 | 4/2014 | Matsumoto |
| 8,702,690 B2 | 4/2014 | Paul et al. |
| 8,709,008 B2 | 4/2014 | Willis et al. |
| 8,728,077 B2 | 5/2014 | Paul et al. |
| 8,755,860 B2 | 6/2014 | Paul et al. |
| 8,774,906 B2 | 7/2014 | Harks et al. |
| 8,808,281 B2 | 8/2014 | Emmons et al. |
| 8,849,380 B2 | 9/2014 | Patwardhan |
| 8,858,495 B2 | 10/2014 | Tegg et al. |
| 8,876,817 B2 | 11/2014 | Avitall et al. |
| 8,882,697 B2 | 11/2014 | Celermajer et al. |
| 8,894,589 B2 | 11/2014 | Leo et al. |
| 8,894,641 B2 | 11/2014 | Brannan |
| 8,900,219 B2 | 12/2014 | Sinofsky et al. |
| 8,900,225 B2 | 12/2014 | Bar-Tal et al. |
| 8,900,228 B2 | 12/2014 | Grunewald et al. |
| 8,900,229 B2 | 12/2014 | Govari et al. |
| 8,906,011 B2 | 12/2014 | Gelbart et al. |
| 8,915,878 B2 | 12/2014 | Winkler et al. |
| 8,923,959 B2 | 12/2014 | Boveja et al. |
| 8,926,604 B2 | 1/2015 | Govari et al. |
| 8,929,973 B1 | 1/2015 | Webb et al. |
| 8,948,851 B2 | 2/2015 | Leblond et al. |
| 8,951,247 B2 | 2/2015 | Ding et al. |
| 8,986,292 B2 | 3/2015 | Sliwa et al. |
| 8,986,298 B2 | 3/2015 | Lee et al. |
| 8,998,890 B2 | 4/2015 | Paul et al. |
| 8,998,892 B2 | 4/2015 | Winkler et al. |
| 8,998,893 B2 | 4/2015 | Avitall |
| 9,008,746 B2 | 4/2015 | Pastore et al. |
| 9,014,789 B2 | 4/2015 | Mercader et al. |
| 9,084,611 B2 | 7/2015 | Amirana et al. |
| 9,087,368 B2 | 7/2015 | Tearney et al. |
| 9,186,066 B2 | 11/2015 | Tearney et al. |
| 9,220,411 B2 | 12/2015 | Hillman |
| 9,233,241 B2 | 1/2016 | Long |
| 9,277,865 B2 | 3/2016 | Yamaguchi et al. |
| 10,076,238 B2 | 9/2018 | Amirana et al. |
| 10,143,517 B2 | 12/2018 | Ransbury et al. |
| 10,568,535 B2 | 2/2020 | Roberts et al. |
| 10,682,179 B2 | 6/2020 | Ransbury et al. |
| 10,716,462 B2 | 7/2020 | Amirana et al. |
| 10,722,301 B2 | 7/2020 | Amirana et al. |
| 10,736,512 B2 | 8/2020 | Mercader et al. |
| 10,779,904 B2 | 9/2020 | Ransbury et al. |
| 11,096,584 B2 | 8/2021 | Mercader et al. |
| 11,457,817 B2 | 10/2022 | Sarvazyan |
| 11,559,192 B2 | 1/2023 | Amirana et al. |
| 11,559,352 B2 | 1/2023 | Amirana et al. |
| 2002/0042556 A1 | 4/2002 | Sugimoto et al. |
| 2002/0123666 A1 | 9/2002 | Matsumoto |
| 2002/0143326 A1 | 10/2002 | Foley et al. |
| 2003/0028188 A1 | 2/2003 | Paddock et al. |
| 2003/0120142 A1 | 6/2003 | Dubuc et al. |
| 2003/0120144 A1 | 6/2003 | Grabek et al. |
| 2003/0125719 A1 | 7/2003 | Furnish |
| 2003/0208252 A1 | 11/2003 | O' Boyle et al. |
| 2004/0073206 A1 | 4/2004 | Foley et al. |
| 2004/0092806 A1 | 5/2004 | Sagon et al. |
| 2004/0097788 A1* | 5/2004 | Mourlas .................. A61B 1/05 600/116 |
| 2004/0138656 A1 | 7/2004 | Francischelli et al. |
| 2004/0187875 A1 | 9/2004 | He et al. |
| 2004/0215310 A1 | 10/2004 | Amirana |
| 2004/0267326 A1 | 12/2004 | Ocel et al. |
| 2005/0014995 A1 | 1/2005 | Amundson et al. |
| 2005/0043637 A1 | 2/2005 | Caplan et al. |
| 2005/0070987 A1 | 3/2005 | Erickson |
| 2005/0075629 A1 | 4/2005 | Chapelon et al. |
| 2005/0119523 A1 | 6/2005 | Starksen et al. |
| 2005/0119548 A1 | 6/2005 | Lin et al. |
| 2005/0197530 A1 | 9/2005 | Wallace et al. |
| 2005/0197623 A1 | 9/2005 | Leeflang et al. |
| 2005/0215899 A1 | 9/2005 | Trahey et al. |
| 2005/0228452 A1 | 10/2005 | Mourlas et al. |
| 2005/0251125 A1 | 11/2005 | Pless et al. |
| 2005/0283195 A1 | 12/2005 | Pastore et al. |
| 2006/0009756 A1 | 1/2006 | Francischelli et al. |
| 2006/0013454 A1 | 1/2006 | Flewelling et al. |
| 2006/0025760 A1 | 2/2006 | Podhajsky |
| 2006/0089636 A1 | 4/2006 | Christopherson et al. |
| 2006/0122583 A1 | 6/2006 | Pesach et al. |
| 2006/0122587 A1 | 6/2006 | Sharareh |
| 2006/0184048 A1 | 8/2006 | Saadat |
| 2006/0229515 A1 | 10/2006 | Sharareh et al. |
| 2006/0229594 A1 | 12/2006 | Franchichelli et al. |
| 2006/0278246 A1 | 12/2006 | Eng et al. |
| 2007/0015964 A1 | 1/2007 | Eversull et al. |
| 2007/0016079 A1 | 1/2007 | Freeman et al. |
| 2007/0016130 A1 | 1/2007 | Leeflang et al. |
| 2007/0038126 A1 | 2/2007 | Pyle et al. |
| 2007/0049827 A1 | 3/2007 | Donaldson et al. |
| 2007/0083217 A1 | 4/2007 | Eversull et al. |
| 2007/0167828 A1 | 7/2007 | Saadat |
| 2007/0179487 A1 | 8/2007 | Tearney et al. |
| 2007/0185479 A1 | 8/2007 | Lau |
| 2007/0225697 A1 | 9/2007 | Shroff et al. |
| 2007/0270717 A1 | 11/2007 | Tang et al. |
| 2007/0270789 A1 | 11/2007 | Berger |
| 2007/0270792 A1 | 11/2007 | Hennemann et al. |
| 2007/0270795 A1 | 11/2007 | Francischelli et al. |
| 2007/0276259 A1 | 11/2007 | Okawa et al. |
| 2007/0287886 A1 | 12/2007 | Saadat |
| 2007/0293724 A1 | 12/2007 | Saadat et al. |
| 2008/0009747 A1 | 1/2008 | Saadat et al. |
| 2008/0015569 A1 | 1/2008 | Saadat et al. |
| 2008/0021275 A1 | 1/2008 | Tearney et al. |
| 2008/0033241 A1 | 2/2008 | Peh et al. |
| 2008/0058650 A1 | 3/2008 | Saadat et al. |
| 2008/0058785 A1 | 3/2008 | Boyden et al. |

(56) References Cited

U.S. PATENT DOCUMENTS

| | | |
|---|---|---|
| 2008/0058786 A1 | 3/2008 | Boyden et al. |
| 2008/0097476 A1 | 4/2008 | Peh et al. |
| 2008/0101677 A1 | 5/2008 | Mashke et al. |
| 2008/0103355 A1 | 5/2008 | Boyden et al. |
| 2008/0119694 A1 | 5/2008 | Lee |
| 2008/0125634 A1 | 5/2008 | Ryan et al. |
| 2008/0154257 A1 | 6/2008 | Sharareh et al. |
| 2008/0172049 A1 | 7/2008 | Bredno et al. |
| 2008/0183036 A1 | 7/2008 | Saadat et al. |
| 2008/0212867 A1 | 9/2008 | Provenzano et al. |
| 2008/0214889 A1 | 9/2008 | Saadat et al. |
| 2008/0221448 A1 | 9/2008 | Khuri-Yakub et al. |
| 2008/0228032 A1 | 9/2008 | Starksen et al. |
| 2008/0228079 A1 | 9/2008 | Donaldson et al. |
| 2008/0243214 A1 | 10/2008 | Koblish |
| 2008/0275300 A1 | 11/2008 | Rothe et al. |
| 2008/0281293 A1 | 11/2008 | Peh et al. |
| 2008/0300589 A1 | 12/2008 | Paul et al. |
| 2009/0012367 A1 | 1/2009 | Chin et al. |
| 2009/0030276 A1 | 1/2009 | Saadat et al. |
| 2009/0030412 A1 | 1/2009 | Willis et al. |
| 2009/0054803 A1 | 2/2009 | Saadat et al. |
| 2009/0062790 A1 | 3/2009 | Malchano et al. |
| 2009/0076373 A1 | 3/2009 | Maschke |
| 2009/0076375 A1 | 3/2009 | Maschke |
| 2009/0082623 A1 | 3/2009 | Rothe et al. |
| 2009/0082660 A1 | 3/2009 | Rahn et al. |
| 2009/0125022 A1 | 5/2009 | Saadat et al. |
| 2009/0131931 A1 | 5/2009 | Lee et al. |
| 2009/0143640 A1 | 6/2009 | Saadat et al. |
| 2009/0203962 A1 | 8/2009 | Miller et al. |
| 2009/0204069 A1 | 8/2009 | Hirszowicz et al. |
| 2009/0221871 A1 | 9/2009 | Peh et al. |
| 2009/0227999 A1 | 9/2009 | Willis et al. |
| 2009/0253991 A1 | 10/2009 | Balas et al. |
| 2009/0275799 A1 | 11/2009 | Saadat et al. |
| 2009/0281541 A1 | 11/2009 | Ibrahim et al. |
| 2009/0292211 A1 | 11/2009 | Lin et al. |
| 2009/0299354 A1 | 12/2009 | Melsky et al. |
| 2009/0299363 A1 | 12/2009 | Saadat et al. |
| 2009/0306643 A1 | 12/2009 | Pappone et al. |
| 2010/0022832 A1 | 1/2010 | Makiyama |
| 2010/0041986 A1 | 2/2010 | Nguyen et al. |
| 2010/0056966 A1 | 3/2010 | Toth |
| 2010/0081127 A1 | 4/2010 | Maier et al. |
| 2010/0081873 A1 | 4/2010 | Tanimura et al. |
| 2010/0081948 A1 | 4/2010 | Pastore et al. |
| 2010/0084563 A1 | 4/2010 | Ohno |
| 2010/0114094 A1 | 5/2010 | Thapliyal et al. |
| 2010/0130836 A1 | 5/2010 | Malchano et al. |
| 2010/0152728 A1 | 6/2010 | Park et al. |
| 2010/0198065 A1 | 8/2010 | Thapliyal et al. |
| 2010/0204544 A1 | 8/2010 | Takei |
| 2010/0204561 A1 | 8/2010 | Saadat |
| 2010/0228247 A1 | 9/2010 | Paul et al. |
| 2010/0241117 A1 | 9/2010 | Paul et al. |
| 2010/0274364 A1 | 10/2010 | Pacanowsky |
| 2010/0312094 A1 | 12/2010 | Guttman et al. |
| 2010/0312096 A1 | 12/2010 | Guttman et al. |
| 2010/0331838 A1 | 12/2010 | Ibrahim et al. |
| 2011/0009793 A1 | 1/2011 | Lucero |
| 2011/0019893 A1 | 1/2011 | Rahn et al. |
| 2011/0029058 A1 | 2/2011 | Swanson |
| 2011/0042580 A1 | 2/2011 | Wilson et al. |
| 2011/0066147 A1 | 3/2011 | He et al. |
| 2011/0071647 A1 | 3/2011 | Mahon |
| 2011/0082450 A1 | 4/2011 | Melsky et al. |
| 2011/0082451 A1 | 4/2011 | Melsky et al. |
| 2011/0082452 A1 | 4/2011 | Melsky et al. |
| 2011/0117025 A1 | 5/2011 | Dacosta et al. |
| 2011/0144524 A1 | 6/2011 | Fish et al. |
| 2011/0224494 A1 | 9/2011 | Piskun et al. |
| 2011/0230903 A1 | 9/2011 | Bertolero |
| 2011/0275932 A1 | 11/2011 | Leblond et al. |
| 2011/0276046 A1 | 11/2011 | Heimbecher et al. |
| 2011/0282250 A1 | 11/2011 | Fung et al. |
| 2011/0313417 A1 | 12/2011 | De La Rama et al. |
| 2012/0023638 A1 | 2/2012 | Leicester |
| 2012/0029504 A1 | 2/2012 | Afonso et al. |
| 2012/0109031 A1 | 5/2012 | Vollbrecht |
| 2012/0123276 A1 | 5/2012 | Govari et al. |
| 2012/0143177 A1 | 6/2012 | Avitall |
| 2012/0150046 A1 | 6/2012 | Watson et al. |
| 2012/0184812 A1 | 7/2012 | Terakawa |
| 2012/0184813 A1 | 7/2012 | Terakawa |
| 2012/0197243 A1* | 8/2012 | Sherman ............... A61B 18/12 606/32 |
| 2012/0215112 A1 | 8/2012 | Lewis et al. |
| 2012/0220999 A1 | 8/2012 | Long |
| 2012/0259263 A1 | 10/2012 | Celermajer et al. |
| 2012/0323237 A1 | 12/2012 | Paul et al. |
| 2012/0326055 A1 | 12/2012 | Wilson et al. |
| 2013/0006116 A1 | 1/2013 | Kim et al. |
| 2013/0023865 A1 | 1/2013 | Steinke et al. |
| 2013/0030425 A1 | 1/2013 | Stewart et al. |
| 2013/0079645 A1 | 3/2013 | Amirana et al. |
| 2013/0085416 A1 | 4/2013 | Mest |
| 2013/0096593 A1 | 4/2013 | Thapliyal et al. |
| 2013/0096594 A1 | 4/2013 | Thapliyal et al. |
| 2013/0102862 A1 | 4/2013 | Amirana et al. |
| 2013/0107002 A1 | 5/2013 | Kikuchi |
| 2013/0137949 A1 | 5/2013 | Freeman et al. |
| 2013/0150693 A1 | 6/2013 | D'Angelo et al. |
| 2013/0150732 A1 | 6/2013 | Manzke et al. |
| 2013/0158545 A1 | 6/2013 | Govari et al. |
| 2013/0172742 A1 | 7/2013 | Rankin et al. |
| 2013/0172875 A1 | 7/2013 | Govari et al. |
| 2013/0226163 A1 | 8/2013 | Peled et al. |
| 2013/0237841 A1 | 9/2013 | Freeman et al. |
| 2013/0253330 A1 | 9/2013 | Demos |
| 2013/0261455 A1 | 10/2013 | Thapliyal et al. |
| 2013/0267875 A1 | 10/2013 | Thapliyal et al. |
| 2013/0281920 A1 | 10/2013 | Hawkins et al. |
| 2013/0282005 A1 | 10/2013 | Koch et al. |
| 2013/0289358 A1 | 10/2013 | Melsky et al. |
| 2013/0289672 A1 | 10/2013 | Hakomori et al. |
| 2013/0296840 A1 | 11/2013 | Condie et al. |
| 2013/0310680 A1 | 11/2013 | Werahera et al. |
| 2013/0331831 A1 | 12/2013 | Werneth et al. |
| 2014/0031802 A1 | 1/2014 | Melsky |
| 2014/0058244 A1 | 2/2014 | Krocak |
| 2014/0058246 A1 | 2/2014 | Boveja et al. |
| 2014/0081253 A1 | 3/2014 | Kumar et al. |
| 2014/0088418 A1 | 3/2014 | Radulescu et al. |
| 2014/0107430 A1 | 4/2014 | Deno et al. |
| 2014/0121537 A1 | 5/2014 | Aeby et al. |
| 2014/0121660 A1 | 5/2014 | Hauck |
| 2014/0148703 A1 | 5/2014 | Deladi et al. |
| 2014/0163360 A1 | 6/2014 | Stevens-Wright et al. |
| 2014/0163543 A1 | 6/2014 | Allison et al. |
| 2014/0171806 A1 | 6/2014 | Govari et al. |
| 2014/0171936 A1 | 6/2014 | Govari et al. |
| 2014/0180273 A1 | 6/2014 | Nair |
| 2014/0194867 A1 | 7/2014 | Fish et al. |
| 2014/0194869 A1 | 7/2014 | Leo et al. |
| 2014/0243843 A1 | 8/2014 | Havel et al. |
| 2014/0275972 A1 | 9/2014 | George et al. |
| 2014/0276687 A1 | 9/2014 | Goodman et al. |
| 2014/0276771 A1 | 9/2014 | Miller et al. |
| 2014/0316280 A1 | 10/2014 | Mueller et al. |
| 2014/0324085 A1 | 10/2014 | Thapliyal et al. |
| 2014/0350547 A1 | 11/2014 | Sharareh et al. |
| 2014/0357956 A1 | 12/2014 | Salahieh et al. |
| 2014/0378846 A1 | 12/2014 | Hosoda et al. |
| 2015/0038824 A1 | 2/2015 | Lupotti |
| 2015/0073245 A1 | 3/2015 | Klimovitch et al. |
| 2015/0099979 A1* | 4/2015 | Caves .................. A61B 5/0071 600/407 |
| 2015/0141847 A1 | 5/2015 | Sarvazyan et al. |
| 2015/0164332 A1 | 6/2015 | Mercader et al. |
| 2015/0182279 A1 | 7/2015 | Ashton et al. |
| 2015/0196202 A1* | 7/2015 | Mercader ............. A61B 5/0071 600/478 |
| 2015/0327753 A1 | 11/2015 | Amirana et al. |

(56) References Cited

U.S. PATENT DOCUMENTS

| | | |
|---|---|---|
| 2015/0346100 A1 | 12/2015 | Racowsky et al. |
| 2016/0051321 A1 | 2/2016 | Salahieh et al. |
| 2016/0120599 A1* | 5/2016 | Amirana ............... A61B 90/37 606/34 |
| 2016/0120602 A1 | 5/2016 | Ransbury et al. |
| 2016/0143522 A1 | 5/2016 | Ransbury et al. |
| 2016/0228206 A1 | 8/2016 | Bell et al. |
| 2017/0014202 A1 | 1/2017 | Ransbury et al. |
| 2017/0020394 A1 | 1/2017 | Harrington |
| 2017/0135559 A1 | 5/2017 | Horrisberger et al. |
| 2018/0263476 A1 | 9/2018 | Amirana et al. |
| 2019/0053849 A1 | 2/2019 | Ransbury et al. |
| 2020/0008681 A1 | 1/2020 | Sarvazyan |
| 2020/0330727 A1 | 10/2020 | Creighton |
| 2020/0352425 A1 | 11/2020 | Amirana et al. |
| 2020/0352644 A1 | 11/2020 | Ransbury et al. |
| 2020/0352645 A1 | 11/2020 | Amirana et al. |
| 2021/0045834 A1 | 2/2021 | Amirana et al. |
| 2021/0205017 A1 | 7/2021 | Amirana et al. |
| 2021/0369118 A1 | 12/2021 | Sarvazyan |
| 2022/0031377 A1 | 2/2022 | Ransbury et al. |
| 2022/0133172 A1 | 5/2022 | Ransbury et al. |
| 2022/0142482 A1 | 5/2022 | Mercader et al. |
| 2022/0226665 A1 | 7/2022 | Uto |
| 2023/0293000 A1 | 9/2023 | Amirana et al. |
| 2023/0404373 A1 | 12/2023 | Ransbury et al. |

FOREIGN PATENT DOCUMENTS

| | | |
|---|---|---|
| CN | 101199410 | 6/2008 |
| CN | 102099671 | 6/2011 |
| CN | 102397104 | 4/2012 |
| CN | 203525125 | 4/2014 |
| CN | 106028914 | 10/2016 |
| DE | 102005021205 | 11/2006 |
| DE | 102011083522 | 3/2013 |
| EP | 2691041 | 2/2014 |
| EP | 2 889 013 | 7/2015 |
| JP | 60182928 | 9/1985 |
| JP | 63-262613 | 10/1988 |
| JP | 10150177 | 6/1998 |
| JP | 2006158546 | 6/2006 |
| JP | 20090148550 A | 7/2009 |
| JP | 2011/212423 | 10/2011 |
| JP | 201252882 A | 3/2012 |
| JP | 20130544551 A | 12/2013 |
| JP | 20150128586 A | 7/2015 |
| NL | 2002010 | 10/2009 |
| WO | WO 1997/037622 | 10/1997 |
| WO | WO 1999/013934 | 3/1999 |
| WO | WO 2001/001854 | 1/2001 |
| WO | WO 2001/072214 | 10/2001 |
| WO | WO 2003/092520 | 11/2003 |
| WO | WO 2004/028353 | 4/2004 |
| WO | WO 2006/028824 | 3/2006 |
| WO | 2007041542 A2 | 4/2007 |
| WO | WO 2007/109554 | 9/2007 |
| WO | WO 2007/127228 | 11/2007 |
| WO | WO 2008/028149 | 3/2008 |
| WO | 2008054423 A1 | 5/2008 |
| WO | WO 2008/114748 | 9/2008 |
| WO | WO 2008/154578 | 12/2008 |
| WO | WO 2010/075450 | 7/2010 |
| WO | WO 2011/025640 | 3/2011 |
| WO | WO 2011/113162 | 9/2011 |
| WO | WO 2012038824 | 3/2012 |
| WO | WO 2012/049621 | 4/2012 |
| WO | WO 2012/067682 | 5/2012 |
| WO | 20120131577 A2 | 10/2012 |
| WO | WO 2013/044182 | 3/2013 |
| WO | WO 2013/068885 | 5/2013 |
| WO | WO 2013/116316 | 8/2013 |
| WO | WO 2013/169340 | 11/2013 |
| WO | WO 2014/028770 | 2/2014 |
| WO | 2014205256 A2 | 12/2014 |
| WO | WO 2015/073871 | 5/2015 |
| WO | WO 2015/077474 | 5/2015 |
| WO | WO 2016/073476 | 5/2016 |
| WO | WO 2016/073492 | 5/2016 |
| WO | WO 2016/086160 | 6/2016 |
| WO | WO 2017/015257 | 1/2017 |

OTHER PUBLICATIONS

Anderson, J.K., "Time Course of Nicotinamide Adenine Dinucleotide Diaphorase Staining after Renal Radiofrequency Ablation Influences Viability Assessment", Journal of Endourology, vol. 21, Issue 2, Mar. 5, 2007.

Asfour et al, "Signal decomposition of transmembrane voltage-sensitive dye fluorescence using a multiresolution wavelet analysis" IEEE Trans Biomed Eng. 2011; 58: 2083-2093.

Berthier, J.P., et al., "XeCl Laser Action at Medium Fluences on Biological Tissues: Fluorescence Study and Simulation with a Chemical Solution", Journal of Photochemistry and Photobiology B: Biology, vol. 5, Issues 3-4, pp. 495-503, May 1990.

Bogaards et al., In Vivo Quantification of Fluorescent Molecular Markers in Real-Time: A Review to Evaluate the Performance of Five Existing Methods, Photodiagnosis and Photodynamic Therapy, vol. 4: 170-178 (2007).

Bogaards et al., n Vivo Quantification of Fluorescent Molecular Markers in Real-Time by Ratio Imaging for Diagnostic Screening and Image-Guided Surgery, Lasers in Surgery and Medicing vol. 39: 605-613 (2007).

Coremans et al, "Pretransplantation assessment of renal viability with NADH fluorimetry", Kidney International, vol. 57, (2000), pp. 671-683.

Demos et al, "Real time assessment of RF cardiac tissue ablation with optical spectroscopy", Opt Express. 2008; 16: 15286-15296.

Dickfeld et al, "Characterization of Radiofrequency Ablation Lesions With Gadolinium-Enhanced Cardiovascular Magnetic Resonance Imaging" J Am Coll Cardiol. 2006; 47: 370-378.

Dukkipati et al, "Visual balloon-guided point-by-point ablation: reliable, reproducible, and persistent pulmonary vein isolation", Circ Arrhythm Electrophysiol. 2010; 3: 266-273.

Dyer, B., et al., Heart, "The Application of Autofluorescence Lifetime Metrology as a Novel Label-free Technique for the Assessment of Cardiac Disease", vol. 11, Issue Supplement 3, pp. 186, Jun. 2014.

Fleming et al, "Real-time monitoring of cardiac redio-frequency ablation lesion formation using an optical coherence tomography forward-imaging catheter", Journal of Biomedical Optics, May/Jun. 2010, vol. 15(3).

Fleming et al, "Toward guidance of epicardial cardiac radiofrequency ablation therapy using optical coherence tomography" J Biomed Opt. 2010; 15: 041510.

Kalman, J.M., et al., "Cardiac Magnetic Resonance Imaging to Detect Non-Contiguous Scar Following Atrial Fibrillation Ablation: Identifying our Knowledge Gaps", European Heart Journal, Editorial, pp. 1-3, Feb. 26, 2014.

Kay et al, "Locations of ectopic beats coincide with spatial gradients of NADH in a regional model of low-flow reperfusion", Am J Physiol Heart Circ Physiol. 2008; 294: H2400-5.

Khoury et al., "Localizing and Quantifying Ablation Lesions in the Left Ventricle by Myocardial Contrast Echocardiography", J Cardiovasc Electrophysiol. 2004; 15: 1078-1087.

Lardo, et al "Visualization and temporal/spatial characterization of cardiac radiofrequency ablation lesions using magnetic resonance imaging", Circulation. 2000; 102: 698-705.

Li, "Multiphoton Microscopy of Live Tissues with Ultraviolet Autofluorescence", IEEE Journal of Selected Topic in Quantam Electronics , May/Jun. 2010, vol. 16, Issue 3, pp. 516-513.

Lo et al, "Three-dimensional electroanatomic mapping systems in catheter ablation of atrial fibrillation", Circ J. 2010; 74: 18-23.

Mayevsky et al. "Oxidation-reduction states of NADH in vivo: from animals to clinical use", Mitochondrion. 2007; 7: 330-339.

(56) References Cited

OTHER PUBLICATIONS

Mercader et al, "NADH as an Endogenous Marker of Cardiac Tissue Injury at the Site of Radiofrequency Ablation", The George Washington University, Washington DC, Mar. 18, 2011.

Mercader et al, "Use of endogenous NADH fluorescence for real-time in situ visualization of epicardial radiofrequency ablation lesions and gaps", Am J Physiol Heart Circ Physiol, May 2012; 302(10): H2131-H2138.

Naito, H., et al., "Use of Nadh Fluorescence Imaging for Early Detection of Energy Failure and a Prediction of Infarction", Critical Care Medicine, vol. 39, Issue 12, pp. 40, Dec. 2011.

Ranji et al, "Quantifying Acute Myocardial Injury Using Ratiometric Fluorometry", IEEE Trans Biomed Eng. May 2009, 56(5): 1556-1563.

Riess et al, "Altered NADH and improved function by anesthetic and ischemic preconditioning in guinea pig intact hearts", Am J Physiol Heart Circ Physiol 283; H53-H60, Mar. 14, 2002.

Smith, S., et al., "Imaging Appearances Following Thermal Ablation", Clinical Radiology, vol. 63, Issue 1, pp. 1-11, Jan. 2008.

Sra, J., et al., "Computed Tomography-Fluoroscopy Image Integration-Guided Catheter Ablation of Atrial Fibrillation", Journal of Cardiovascular Electrophysiology, vol. 18, Issue 4, pp. 409-414, Apr. 2007.

Swartling et al, "Changes in tissue optical properties due to radiofrequency ablation of myocardium", Med Biol Eng Comput. 2003; 41: 403-409.

Vo-Dinh et al., "A Hyperspectral Imaging System for In Vivo Optical Diagnostics", IEEE Engineering in Medicine and Biology Magazine, pp. 40-49, Sep./Oct. 2004.

Weight, C.J., et al., "Correlation of Radiographic Imaging and Histopathology Following Cryoablation and Radio Frequency Ablation for Renal Tumors", The Journal of Urology, vol. 179, Issue 4, pp. 1277-1283, Apr. 2008.

International Search Report based on PCT/US2021/012836 dated Apr. 1, 2021.

* cited by examiner

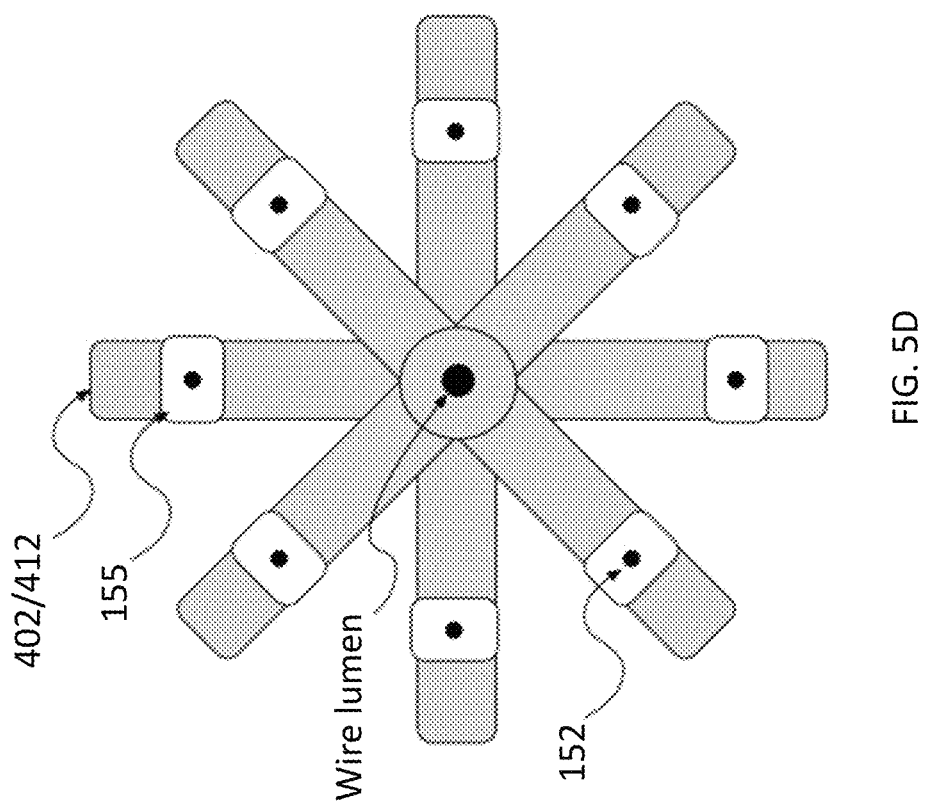

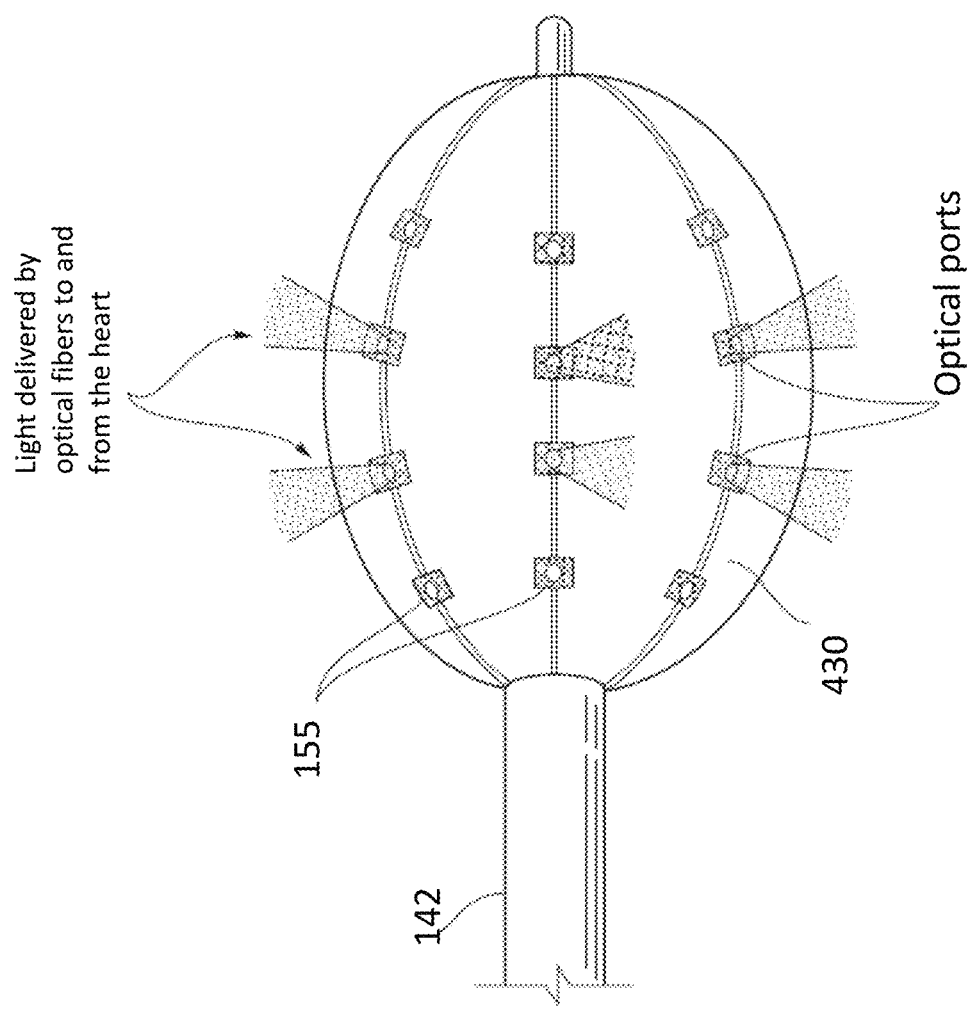

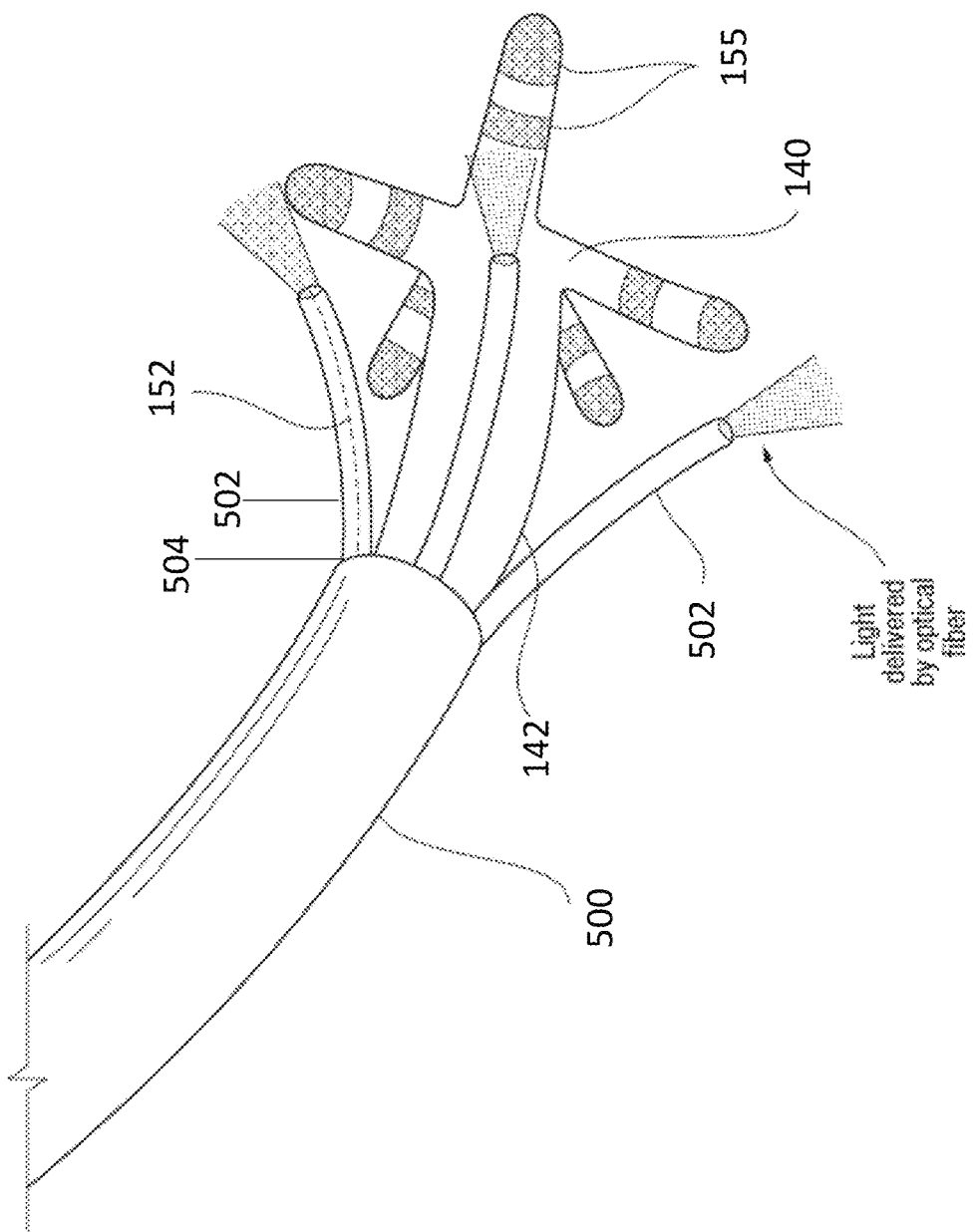

SYSTEMS AND METHODS FOR OPTICAL INTERROGATION OF ABLATION LESIONS

RELATED APPLICATIONS

This application claims the benefit of and priority to U.S. Provisional Application Ser. No. 62/958,419, filed on Jan. 8, 2020, which is incorporated herein by reference in its entirety.

FIELD

The present disclosure generally relates to ablation and optical tissue interrogation systems and methods to optically interrogate tissue to assess impact of energy delivery to the tissue and to assess quality of contact between a catheter and tissue.

BACKGROUND

Atrial fibrillation (AF) is the most common sustained arrhythmia in the world, which currently affects millions of people. In the United States, AF is projected to affect 10 million people by the year 2050. AF is associated with increased mortality, morbidity, and an impaired quality of life, and is an independent risk factor for stroke. The substantial lifetime risk of developing AF underscores the public health burden of the disease, which in the U.S. alone amounts to an annual treatment cost exceeding $7 billion.

Most episodes in patients with AF are known to be triggered by focal electrical activity originating from within muscle sleeves that extend into the Pulmonary Veins (PV). Atrial fibrillation may also be triggered by focal activity within the superior vena cava or other atrial structures, i.e. other cardiac tissue within the heart's conduction system. These focal triggers can also cause atrial tachycardia that is driven by reentrant electrical activity (or rotors), which may then fragment into a multitude of electrical wavelets that are characteristic of atrial fibrillation. Furthermore, prolonged AF can cause functional alterations in cardiac cell membranes and these changes further perpetuate atrial fibrillation.

Ablation systems are used by physicians to treat atrial fibrillation. Physicians use a catheter to direct energy to either destroy focal triggers or to form electrical isolation lines isolating the triggers from the heart's remaining tissue and conduction system. The latter technique is commonly used in what is called pulmonary vein isolation (PVI). However, the success rate of the AF ablation procedure has remained relatively stagnant with estimates of recurrence to be as high as 30% to 50% one-year post procedure. The most common reason for recurrence after catheter ablation is one or more gaps in the PVI lines. The gaps are usually the result of missed areas or ineffective or incomplete lesions that may temporarily block electrical signals during the procedure but heal over time and facilitate the recurrence of atrial fibrillation.

Ineffective or incomplete lesions are often the result of poor catheter contact with the myocardium. With poor contact the transfer of energy from the catheter to the myocardium is inefficient and often insufficient to cause a proper lesion. Intermittent contact can also be unsafe.

Therefore, there is a need for system and method for forming and verifying ablation lesions to improve outcomes and reduce costs.

SUMMARY

The present disclosure provides systems and methods for performing and monitoring tissue ablation.

In some aspects, the present disclosure provides a system for optical tissue interrogation comprising: a catheter having a plurality of electrodes disposed in an array at a distal end of the catheter, the plurality of electrodes being configured to deliver ablation energy to tissue; and one or more optical fibers extending through the catheter to deliver light from a light source to the tissue and to deliver optical information comprising nicotinamide adenine dinucleotide hydrogen (NADH) fluorescence from the tissue to a sensor, wherein each electrode of the plurality of electrodes is associated with at least one of the one or more optical fibers.

In some embodiments, the light source has at least one wavelength sufficient to excite mitochondrial nicotinamide adenine dinucleotide hydrogen (NADH) in the tissue. In some embodiments, the sensor is configured to receive light having at least one wavelength to detect the NADH fluorescence from the tissue. In some embodiments, the ablation energy is pulsed field ablation energy. In some embodiments, the ablation energy is selected from a group consisting of electroporation energy, radiofrequency energy, microwave energy, electrical energy, electromagnetic energy, cryoenergy, laser energy, ultrasound energy, acoustic energy, chemical energy, and thermal energy. In some embodiments, the light for illuminating the tissue has at least one wavelength between about 300 nm and about 400 nm. In some embodiments, the sensor is configured to receive light having at least one wavelength between about 375 nm and about 650 nm. In some embodiments, each of the plurality of electrodes comprises an optical port and the one or more optical fibers are aligned with the optical port to enable the light to pass through the optical port. In some embodiments, the plurality of electrodes are disposed on an expandable member at the distal end of the catheter.

In some embodiments, the system further comprises a processor in communication with the sensor and configured to generate a digital representation of the NADH fluorescence to distinguish between ablated tissue and non-ablated tissue. In some embodiments, the system further comprises a processor in communication with the sensor and programmed to: obtain the NADH fluorescence from the sensor during ablation of the tissue; generate a digital representation of the NADH fluorescence for monitoring a progression of the ablation of the tissue, wherein a decrease in the NADH fluorescence is indicative of the progression of the ablation of the tissue to enable a user to determine a need for further ablation, and while the tissue is being ablated, monitoring the decrease in the NADH fluorescence and updating the digital representation to show the decrease in the NADH fluorescence throughout the ablation of the tissue. In some embodiments, the optical information is used to predict durability of a lesion in the tissue created by ablating the tissue. In some embodiments, the light and the sensor is configured to receive light having at least one wavelength to detect the collagen fluorescence from the tissue. In some embodiments, the system further comprises a processor in communication with the sensor and configured to generate a digital representation of the collagen fluorescence to assess the fibrotic burden of the tissue.

In some aspects, the present disclosure provides a system for optical tissue interrogation comprising: a light source providing light for illuminating a tissue, the light having at least one wavelength sufficient to excite mitochondrial nicotinamide adenine dinucleotide hydrogen (NADH) in the tissue; a sensor for detecting NADH fluorescence from the tissue, the sensor being configured to receive light having at least one wavelength to detect the NADH fluorescence from the tissue; and a sheath comprising one or more optical fibers extending through the sheath to deliver the light from the light source to the tissue and to deliver optical information frpm the tissue to the sensor, wherein the sheath is configured to receive a catheter therethrough to associate at least one of the one or more optical fibers with an electrode disposed at a distal end of the catheter, the electrode being configured to deliver ablation energy to the tissue.

In some embodiments, the ablation energy is pulsed field ablation energy. In some embodiments, the ablation energy is selected from a group consisting of pulsed filed ablation energy, electroporation energy, radiofrequency energy, microwave energy, electrical energy, electromagnetic energy, cryoenergy, laser energy, ultrasound energy, acoustic energy, chemical energy, and thermal energy. In some embodiments, the light for illuminating the tissue has at least one wavelength between about 300 nm and about 400 nm. In some embodiments, the sensor is configured to receive light having at least one wavelength between about 375 nm and about 650 nm. In some embodiments, the electrode comprises an optical port and the one or more optical fibers are aligned with the optical port to enable the light to pass through the optical port. In some embodiments, the optical information comprises NADH fluorescence.

In some embodiments, the system further comprises a processor in communication with the sensor is configured to generate a digital representation of the NADH fluorescence to distinguish between ablated tissue and non-ablated tissue. In some embodiments, the system further comprises a processor in communication with the sensor and programmed to: obtain the NADH fluorescence from the sensor during ablation of the tissue; generate a digital representation of the NADH fluorescence for monitoring a progression of the ablation of the tissue, wherein a decrease in the NADH fluorescence is indicative of the progression of the ablation of the tissue to enable a user to determine a need for further ablation, and while the tissue is being ablated, monitoring the decrease in the NADH fluorescence and updating the digital representation to show the decrease in the NADH fluorescence throughout the ablation of the tissue.

In some embodiments, the present disclosure provides a system for optical tissue interrogation comprising: a catheter having a plurality of electrodes disposed in an array at a distal end of the catheter; an ablation energy source in communication with the plurality of electrodes for ablating a tissue by one or more electrodes of the plurality of electrodes; a light source providing light for illuminating the tissue, the light having at least one wavelength sufficient to excite mitochondrial nicotinamide adenine dinucleotide hydrogen (NADH) in the tissue; a sensor for detecting NADH fluorescence from the tissue, the sensor being configured to receive light having at least one wavelength to detect the NADH fluorescence from the tissue; and a sheath comprising one or more optical fibers extending through the sheath to deliver the light from the light source to the tissue and to deliver the NADH fluorescence to the sensor, wherein the sheath is configured to receive the catheter therethrough to associate at least one of the one or more optical fibers with an electrode of the plurality of electrodes.

In some embodiments, the ablation energy is pulsed energy ablation energy. In some embodiments, the ablation energy is selected from a group consisting of pulsed filed ablation energy, electroporation energy, radiofrequency energy, microwave energy, electrical energy, electromagnetic energy, cryoenergy, laser energy, ultrasound energy, acoustic energy, chemical energy, and thermal energy. In some embodiments, the light for illuminating the tissue has at least one wavelength between about 300 nm and about 400 nm. In some embodiments, the sensor is configured to receive light having at least one wavelength between about 375 nm and about 650 nm. In some embodiments, the electrode comprises an optical port and the one or more optical fibers are aligned with the optical port to enable the light to pass through the optical port.

In some embodiments, the system further comprises a processor in communication with the sensor is configured to generate a digital representation of the NADH fluorescence to distinguish between ablated tissue and non-ablated tissue. In some embodiments, the system further comprises a processor in communication with the sensor and programmed to: obtain the NADH fluorescence from the sensor during ablation of the tissue; generate a digital representation of the NADH fluorescence for monitoring a progression of the ablation of the tissue, wherein a decrease in the NADH fluorescence is indicative of the progression of the ablation of the tissue to enable a user to determine a need for further ablation, and while the tissue is being ablated, monitoring the decrease in the NADH fluorescence and updating the digital representation to show the decrease in the NADH fluorescence throughout the ablation of the tissue.

In some aspects, the present disclosure provides a system for optical tissue interrogation comprising: a catheter having a plurality of electrodes disposed in an array at a distal end of the catheter, the plurality of electrodes being configured to deliver ablation energy to tissue; and a sheath configured to slidably receive the catheter therethrough, the sheath comprising one or more optical fibers extending through the sheath to deliver light from a light source to the tissue and to deliver nicotinamide adenine dinucleotide hydrogen (NADH) fluorescence from the tissue to a sensor, wherein the sheath is configured to associate each electrode of the plurality of electrodes with at least one of the one or more optical fibers.

In some embodiments, the light source has at least one wavelength sufficient to excite mitochondrial nicotinamide adenine dinucleotide hydrogen (NADH) in the tissue. In some embodiments, the sensor is configured to receive light having at least one wavelength to detect the NADH fluorescence from the tissue. In some embodiments, the ablation energy is pulsed field ablation energy. In some embodiments, the ablation energy is selected from a group consisting of electroporation energy, radiofrequency energy, microwave energy, electrical energy, electromagnetic energy, cryoenergy, laser energy, ultrasound energy, acoustic energy, chemical energy, and thermal energy. In some embodiments, the light for illuminating the tissue has at least one wavelength between about 300 nm and about 400 nm. In some embodiments, the sensor is configured to receive light having at least one wavelength between about 375 nm and about 650 nm. In some embodiments, each of the plurality of electrodes comprises an optical port and the one or more optical fibers are aligned with the optical port to enable the light to pass through the optical port. In some embodiments, a plurality of deflectable extensions extend from the distal end of the sheath, each deflectable arm of the plurality of deflectable arms having a least one optical fiber extending therethrough.

In some embodiments, the system further comprises a processor in communication with the sensor is configured to generate a digital representation of the NADH fluorescence to distinguish between ablated tissue and non-ablated tissue.

In some embodiments, the system further comprises a processor in communication with the sensor and programmed to: obtain the NADH fluorescence from the sensor during ablation of the tissue; generate a digital representation of the NADH fluorescence for monitoring a progression of the ablation of the tissue, wherein a decrease in the NADH fluorescence is indicative of the progression of the ablation of the tissue to enable a user to determine a need for further ablation, and while the tissue is being ablated, monitoring the decrease in the NADH fluorescence and updating the digital representation to show the decrease in the NADH fluorescence throughout the ablation of the tissue.

In some aspects, the present disclosure provides a system for imaging tissue comprising: light source providing light for illuminating a tissue, the light having at least one wavelength sufficient to excite mitochondrial nicotinamide adenine dinucleotide hydrogen (NADH) in the tissue; a sensor for detecting NADH fluorescence from the tissue, the sensor being configured to receive light having at least one wavelength to detect the NADH fluorescence from the tissue; and a sheath comprising one or more optical fibers extending through the sheath to deliver the light from the light source to the tissue and to deliver optical information including the NADH fluorescence to the sensor, wherein the sheath is configured to receive a catheter therethrough to associate at least one of the one or more optical fibers with an electrode disposed at a distal end of the catheter, the electrode being configured to deliver ablation energy to the tissue and, independently movable or steerable arms at the distal end of the sheath being configured to position the optical fibers to be in contact with the tissue to optically interrogate the tissue.

In some embodiments, the present disclosure provides a method for optical tissue interrogation comprising: receiving an NADH fluorescence from a tissue, wherein the tissue is illuminated through one or more optical fibers associated with one or more electrodes configured to deliver ablation energy to the tissue; indicating which electrodes of the one or more electrodes are in contact with the tissue, wherein the ablation energy is delivered only from the electrodes of the one or more electrodes that are in contact with the tissue; and generating a digital representation of the NADH fluorescence for monitoring a progression of the ablation of the tissue.

In some embodiments, a decrease in the NADH fluorescence from the illuminated tissue is indicative of the progression of the ablation of the tissue to enable a user to determine a need for further ablation. In some embodiments, the method further comprises determining, while the tissue is being ablated, a decrease in the detected NADH fluorescence and updating the digital representation to show the decrease in the detected NADH fluorescence throughout the ablation of the tissue. In some embodiments, the ablation energy is pulsed energy ablation energy. In some embodiments, the ablation energy is selected from a group consisting of electroporation energy, radiofrequency energy, microwave energy, electrical energy, electromagnetic energy, cryoenergy, laser energy, ultrasound energy, acoustic energy, chemical energy, and thermal energy. In some embodiments, the tissue is illuminated with light having at least one wavelength between about 300 nm and about 400 nm. In some embodiments, the NADH fluorescence is monitored by detecting light returned from the tissue having at least one wavelength between about 375 nm and about 650 nm. In some embodiments, the one or more of the steps of the present methods is implemented using one or more systems of the present disclosure.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 5D is a distal end view of the expandable members of FIGS. 5A and 5C;

FIG. 7 is an exemplary embodiment of an ablation catheter having an expandable member in the form of a balloon on a distal end thereof;

FIG. 8A-8D are exemplary embodiments of sheaths that include optical components that can be used with ablation catheters;

Figure 1A:
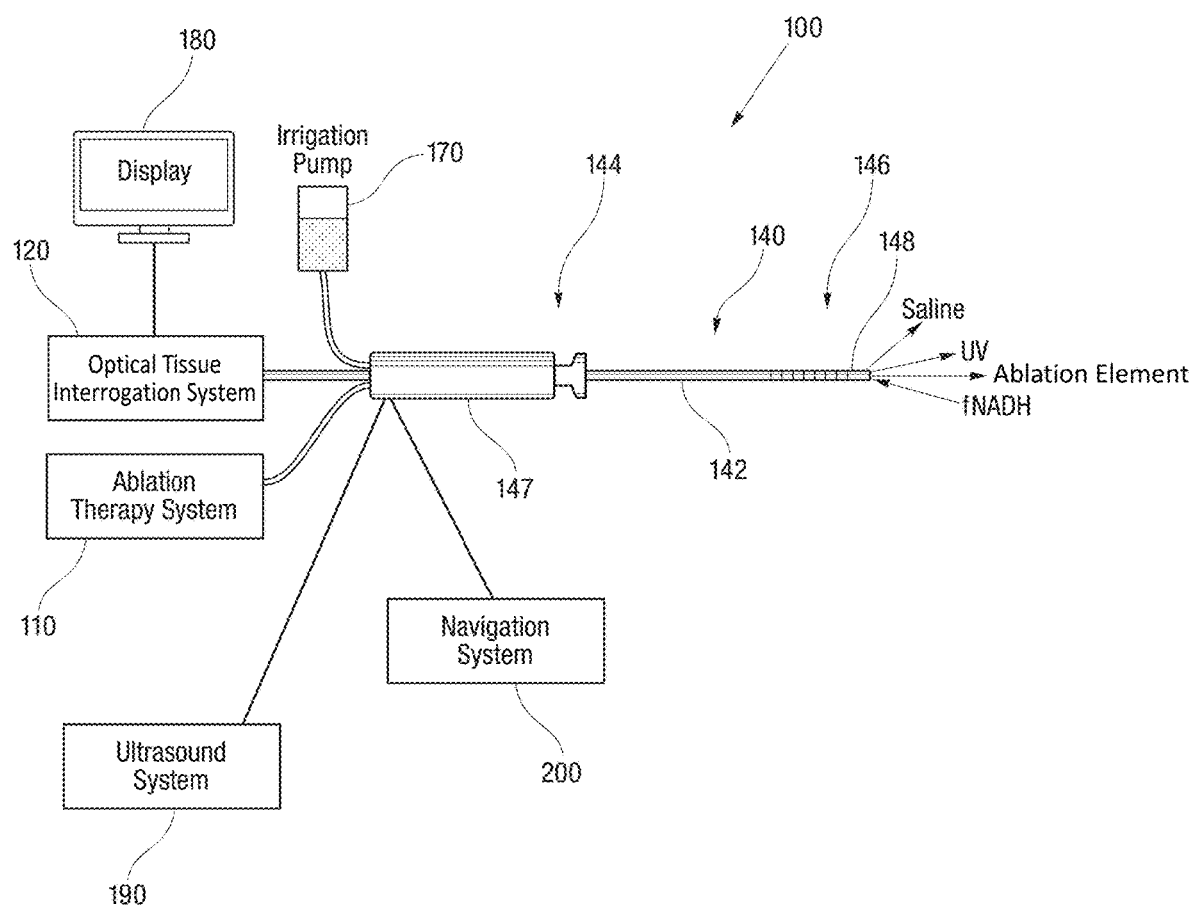
FIG. 1A illustrates an embodiment of an ablation optical tissue interrogation and monitoring system of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The present disclosure provides methods and systems for lesion assessment. In some embodiments, the lesions are formed using ablation energy, for example pulsed field ablation (PFA) energy, to cause lesions through electroporation. In some embodiments, the system of the present disclosure includes a catheter configured to serve two functions: a therapeutic function of delivering ablation therapy (for example, pulsed field ablation) to a target tissue and a diagnostic function of gathering a signature spectrum from a point of contact of the catheter and tissue to access lesions. In some embodiments, the systems and methods of the present disclosure may be employed for imaging tissue using nicotinamide adenine dinucleotide hydrogen (NADH) fluorescence (fNADH). In general, the system may include a catheter with an optical system for exchanging light between tissue and the catheter. In some embodiments, the instant systems allow for direct optical tissue interrogation of the tissue's NADH fluorescence, or lack thereof, induced by ultraviolet (UV) excitation. The NADH fluorescence signature returned from the tissue can be used to determine the impact of the energy on the tissue as well as the quality of contact between the tissue and a catheter system.

In some embodiments, the catheter includes an ablation therapy system to deliver PFA at its distal end and is coupled to a diagnostic unit comprising a light source, such as a laser, and a spectrometer. In some embodiments, the lesion may be formed using a separate catheter or previously formed lesions may be interrogated. The catheter may include one or more fibers extending from the light source and the spectrometer to a distal tip of the catheter to provide illuminating light to the point of contact between the catheter and tissue and to receive and deliver a signature NADH spectrum from the point of contact to the spectrometer. The signature NADH spectrum may be used to assess lesion in the target tissue. In some embodiments, the methods of the present disclosure include illuminating a tissue having a lesion, receiving a signature spectrum of the tissue, and performing a qualitative assessment of the lesion based on the signature spectrum from the tissue. The analysis can occur in real-time before, during and after ablation lesion formation. It should be noted that while the systems and methods of the present disclosure are described in connection with cardiac tissue and NADH spectrum, the systems and methods of the present disclosure may be used in connection with other types of tissue and other types of fluorescence.

System: Diagnostic Unit

In reference to FIG. 1A, the system 100 for providing ablation therapy may include an ablation therapy system 110, a optical tissue interrogation system 120, and a catheter 140. In some embodiments, the system 100 may also include one or more of an irrigation system 170, ultrasound system 190 and a navigation system 200. The system may also include a display 180, which can be a separate display or a part of the optical tissue interrogation system 120, as described below. In some embodiments, the system includes an ablation generator, an irrigation pump 170, an irrigated-tip ablation catheter 140, and the optical tissue interrogation system 120.

Figure 2:
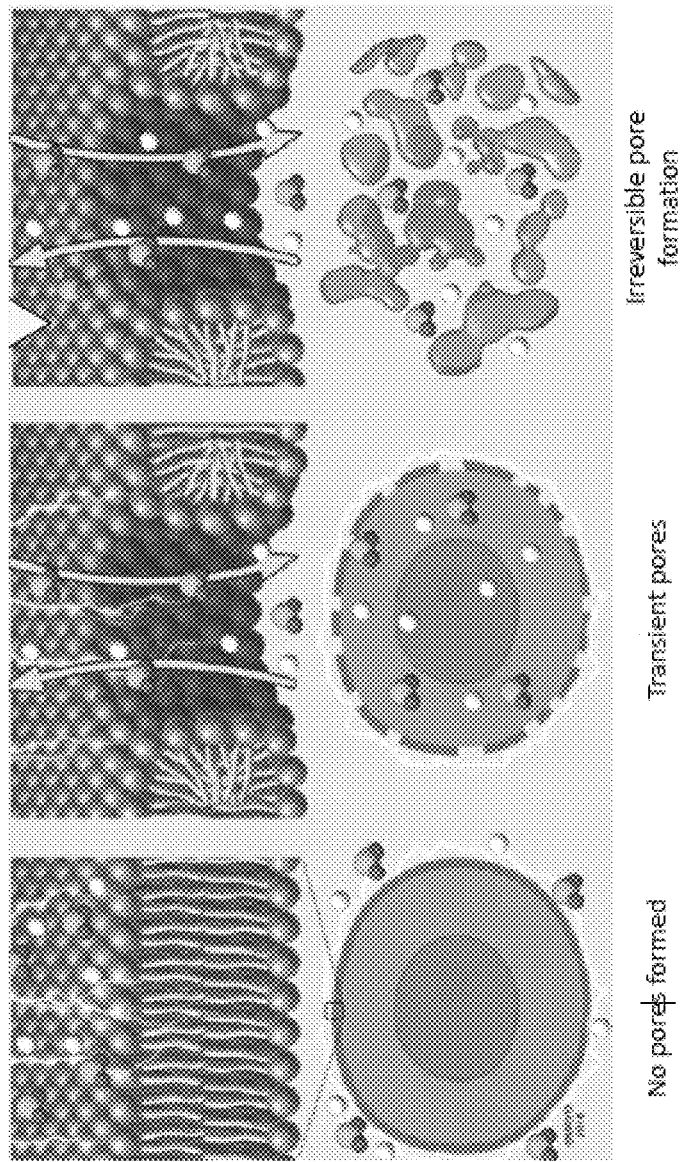
FIG. 2 illustrates cellular response to pulsed field ablation (PFA)

In some embodiments, the ablation therapy system 110 is designed to supply ablation energy to the catheter 140. In some embodiments, the ablation therapy system 110 may include pulsed field ablation (PFA) energy to cause lesions through electroporation. Various systems can be used to deliver PFA energy. As shown in FIG. 2, pulsed electrical field can be modulated and applied to cause irreversible pore formation in cellular membrane that triggers cellular apoptosis. When using PFA energy, a pulse duration is short enough that there is minimal vapor formation, no vapor globe expansion, and no arcing during energy delivery. Exemplary parameter ranges of PFA energy can be 500-3000 V/cm voltage delivered, 1-100 pulses delivered, over a wavelength of microseconds, with a frequency range of 1-5 Hz. The effects of PFA can be almost instantaneous. For example, a single PFA delivery is accomplished within one heartbeat, and typically a lesion can be created with 3-5 PFA deliveries. In addition to or as an alternative to PFA, one or more energy sources that can generate radiofrequency (RF) energy, microwave energy, electrical energy, electromagnetic energy, cryoenergy, laser energy, ultrasound energy, acoustic energy, chemical energy, thermal energy, electroporation energy, or any other type of energy can be used to ablate tissue.

Figure 1B:
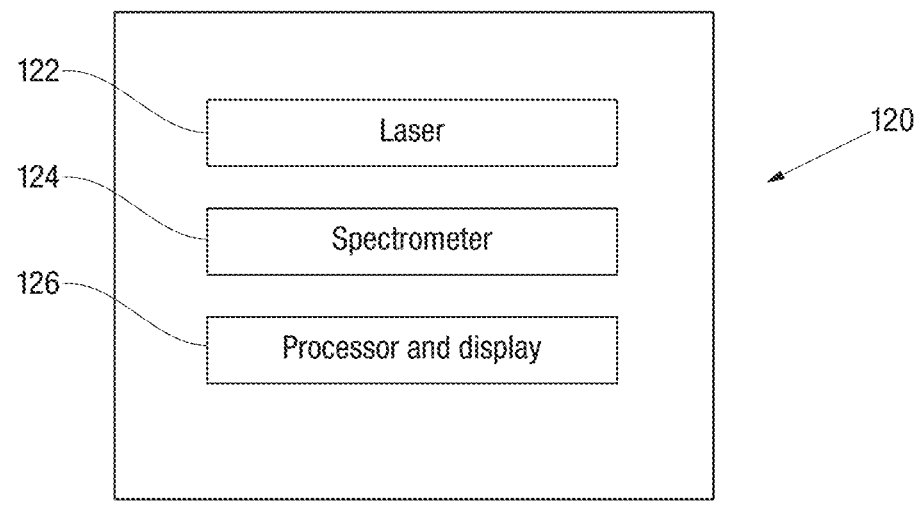
FIG. 1B is a diagram of an embodiment of an optical tissue interrogation system for use in connection with an ablation optical tissue interrogation and monitoring system of the present disclosure.

In reference to FIG. 1B, the optical tissue interrogation system 120 may include a light source 122, a light measuring instrument 124, and a computer system 126.

In some embodiments, the light source 122 may have an output wavelength within the target fluorophore (NADH, in some embodiments) absorption range in order to induce fluorescence in healthy myocardial cells. In some embodiments, the light source 122 is a solid-state laser that can generate UV light to excite NADH fluorescence. In some embodiments, the wavelength may be about 355 nm or 355 nm+/−30 nm. In some embodiments, the light source 122 can be a UV laser. Laser-generated UV light may provide much more power for illumination and may be more efficiently coupled into a fiber-based illumination system, as is used in some embodiments of the catheter 140. In some embodiments, the instant system can use a laser with adjustable power up to 150 mW.

The wavelength range on the light source 122 may be bounded by the anatomy of interest, a user specifically choosing a wavelength that causes maximum NADH fluorescence without exciting excessive fluorescence of collagen, which exhibits an absorption peak at only slightly shorter wavelengths. In some embodiments, the light source 122 generates light having at least one wavelength between 250 nm and 450 nm. In some embodiments, the light source 122 generates light having at least one wavelength between 300 nm and 400 nm. In some embodiments, the light source 122 generates light having at least one wavelength between 330 nm and 385 nm. In some embodiments, the light source 122 generates light having at least one wavelength between 330 nm to 355 nm. In some embodiments, a narrow-band 355 nm source may be used. The output power of the light source 122 may be high enough to produce a recoverable tissue fluorescence signature, yet not so high as to induce cellular damage. The light source 122 may be coupled to an optical fiber to deliver light to and from the catheter 140, as will be described below.

In some embodiments, the systems of the present disclosure may utilize a spectrometer as the light measuring instrument 124, but other light measuring instruments may be employed. The optical fiber can deliver the gathered light to the light measuring instrument 124. The computer system 126 acquires the information from the light measuring instrument 124 and displays it to the physician.

Referring back to FIG. 1A, in some embodiments, the system 100 of the present disclosure may further include an ultrasound system 190. The catheter 140 may be equipped with ultrasound transducers in communication with the ultrasound system 190. In some embodiments, the ultrasound may show tissue depths, which in combination with the metabolic activity or the depth of lesion may be used to determine if a lesion is in fact transmural or not. In some embodiments, the ultrasound transducers may be located in the distal section of the catheter 140, and optionally in the tip of the distal electrode. The ultrasonic transducers may be configured to assess a tissue thickness either below or adjacent to the catheter tip. In some embodiments, the catheter 140 may comprise multiple transducers adapted to provide depth information covering a situation where the catheter tip is relatively perpendicular to a myocardium or relatively parallel to a myocardium.

Figure 3A:
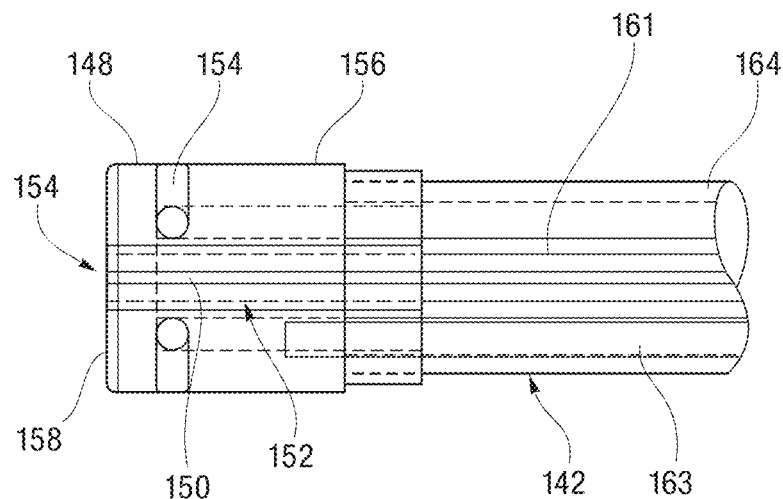
FIGS. 3A, 3B, and 3C illustrate various embodiments of catheters of the present disclosure.

Referring to FIG. 1A, as noted above, the system 100 may also include an irrigation system 170. In some embodiments, the irrigation system 170 pumps saline into the catheter 140 to cool the tip electrode during ablation therapy. This may help to prevent thromboembolism (clots which may or may not move through the bloodstream), steam pops and char formation. In some embodiments, the irrigation fluid is maintained at a positive pressure relative to pressure outside of the catheter 140 for continuous flushing of the one or more openings 154 as shown in FIG. 3A.

Referring to FIG. 1A, the system 100 may also include a navigation system 200 for locating and navigating the catheter 140. In some embodiments, the catheter 140 may include one or more electromagnetic location sensors in communication with the navigation system 200. In some embodiments, the electromagnetic location sensors may be used to locate the tip of the catheter in the navigation system 200. The sensor picks up electromagnetic energy from a source location and computes location through triangulation or other means. In some embodiments, the catheter 140 comprises more than one transducer adapted to render a position of the catheter body 142 and a curvature of the catheter body on a navigation system display. In some embodiments, the navigation system 200 may include one or more magnets and alterations in the magnetic field produced by the magnets on the electromagnetic sensors that can deflect the tip of catheters to the desired direction. Other navigation systems may also be employed, including manual navigation.

Figure 1C:
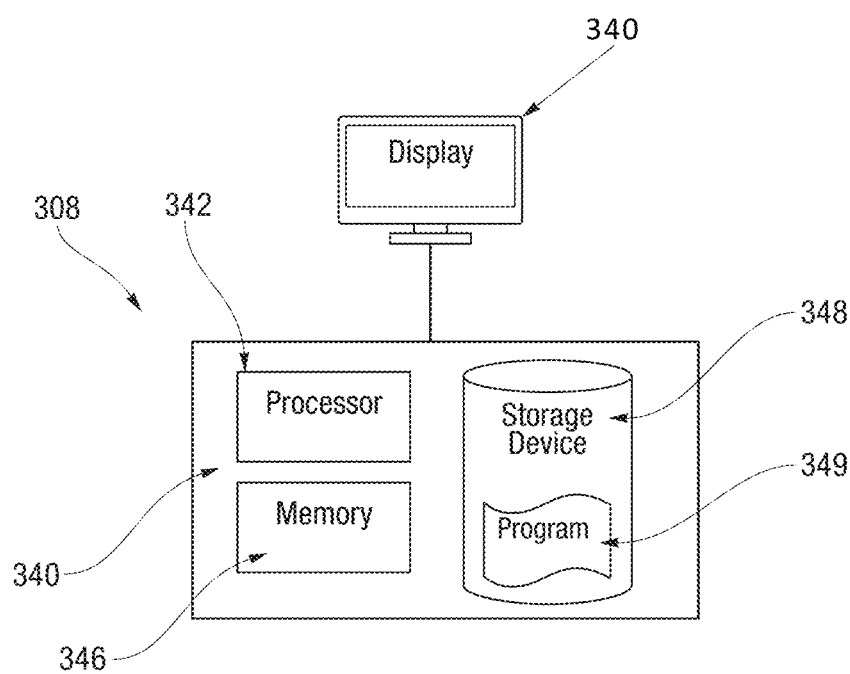
FIG. 1C illustrates an exemplary computer system suitable for use in connection with the systems and methods of the present disclosure.

The computer system 126 can be programed to control various modules of the system 100, including, for example, control over the light source 122, control over the light measuring instrument 124, execution of application specific software, control over ultrasound, navigation and irrigation systems and similar operations. FIG. 1C shows, by way of example, a diagram of a typical processing architecture 308, which may be used in connection with the methods and systems of the present disclosure. A computer processing device 340 can be coupled to display 340AA for graphical output. Processor 342 can be a computer processor 342 capable of executing software. Typical examples can be computer processors (such as Intel® or AMD® processors), ASICs, microprocessors, and the like. Processor 342 can be coupled to memory 346, which can be typically a volatile RAM memory for storing instructions and data while processor 342 executes. Processor 342 may also be coupled to storage device 348, which can be a non-volatile storage medium, such as a hard drive, FLASH drive, tape drive, DVDROM, or similar device. Although not shown, computer processing device 340 typically includes various forms of input and output. The I/O may include network adapters, USB adapters, Bluetooth radios, mice, keyboards, touchpads, displays, touch screens, LEDs, vibration devices, speakers, microphones, sensors, or any other input or output device for use with computer processing device 340. Processor 342 may also be coupled to other types of computer-readable media, including, but not limited to, an electronic, optical, magnetic, or other storage or transmission device capable of providing a processor, such as the processor 342, with computer-readable instructions. Various other forms of computer-readable media can transmit or carry instructions to a computer, including a router, private or public network, or other transmission device or channel, both wired and wireless. The instructions may comprise code from any computer-programming language, including, for example, C, C++, C#, Visual Basic, Java, Python, Perl, and JavaScript.

Program 349 can be a computer program or computer readable code containing instructions and/or data, and can be stored on storage device 348. The instructions may comprise code from any computer-programming language, including, for example, C, C++, C#, Visual Basic, Java, Python, Perl, and JavaScript. In a typical scenario, processor 342 may load some or all of the instructions and/or data of program 349 into memory 346 for execution. Program 349 can be any computer program or process including, but not limited to web browser, browser application, address registration process, application, or any other computer application or process. Program 349 may include various instructions and subroutines, which, when loaded into memory 346 and executed by processor 342 cause processor 342 to perform various operations, some or all of which may effectuate the methods for managing medical care disclosed herein. The program 349 may be stored on any type of non-transitory computer readable medium, such as, without limitation, hard drive, removable drive, CD, DVD or any other type of computer-readable media.

In some embodiments, the computer system may be programmed to perform the steps of the methods of the present disclosure and control various parts of the instant systems to perform necessary operation to achieve the methods of the present disclosure. In some embodiments, the processor may be programed to receive NADH fluorescence data from a tissue illuminated with UV light through the distal tip of the catheter, wherein the tissue is illuminated in a radial direction, an axial direction, or both; to determine from a level of NADH fluorescence in the illuminated tissue when the distal tip of the catheter is in contact with the tissue; and to cause (either automatically or by prompting the user) delivery of ablation energy to the tissue to form a lesion in the tissue upon determining that the distal tip is in contact with the tissue.

The processor may further be programmed for monitoring the level of NADH fluorescence during the delivering ablation energy to confirm that the distal tip remains in contact with the tissue. In some embodiments, monitoring the level of NADH fluorescence during the delivery of ablation energy may be utilized to determine stability of contact between the distal tip and the tissue. In some embodiments, ablation of the tissue may be stopped when the contact between the distal tip and the tissue is not stable. In some embodiments, the processor may further be programmed to collect a spectrum of fluorescence light returned from the illuminated tissue to distinguish tissue type.

In some embodiments, a level of the returned light having a wavelength between about 450 nm and 470 nm is monitored. In some embodiments, the monitored spectrum may be between 420 nm and 500 nm. In some embodiments, the monitored spectrum may be between 400 nm and 520 nm. Additionally or alternatively, a wider spectrum may be monitored, such as, by way of a non-limiting example, between 375 nm and 650 nm. In some embodiments, the NADH fluorescence spectrum and a wider spectrum may be displayed to user simultaneously. In some embodiments, the lesion may be created by ablation PFA energy. In some embodiments, the procedure may be started (by the processor or by prompting the user by the processor) when a NADH fluorescence peak is detected so it can be monitored throughout the procedure. As noted above, the processor may perform these methods in combination with other diagnostic methods, such as ultrasound monitoring.

System: Catheter

In some embodiments, the catheter 140 may be based on a standard ablation catheter with accommodations for the optical fibers for illumination and spectroscopy, as discussed above. In some embodiments, the catheter 140 is a steerable, irrigated ablation catheter (for example, PFA ablation catheter) that can be delivered through a sheath to the endocardial space via a standard transseptal procedure and common access tools. On the handle 147 of the catheter, there may be connections for the standard ablation generator and irrigation system 170 for therapy. The catheter handle 147 also passes the optical fibers that are then connected to the diagnostic unit to obtain the tissue measurements.

Referring back to FIG. 1A, the catheter 140 includes a catheter body 142 having a proximal end 144 and a distal end 146. The catheter body 142 may be made of a biocompatible material, and may be sufficiently flexible to enable steering and advancement of the catheter 140 to a site of ablation. In some embodiments, the catheter body 142 may have zones of variable stiffness. For example, the stiffness of the catheter 140 may increase from the proximal end 144 toward the distal end 146. In some embodiments, the stiffness of the catheter body 142 is selected to enable delivery of the catheter 140 to a desired cardiac location. In some embodiments, the catheter 140 can be a steerable, ablation catheter that can be delivered through a sheath to the endocardial space, and in the case of the heart's left side, via a standard transseptal procedure using common access tools. The catheter 140 may include a handle 147 at the proximal end 144. The handle 147 may be in communication with one or more lumens of the catheter to allow passage of instruments or materials through the catheter 140. In some embodiments, the handle 147 may include connections for the standard PFA generator and irrigation system 170 for therapy. In some embodiments, the catheter 140 may also include one more adaptors configured to accommodate the optical fiber for illumination and spectroscopy.

Figure 3B:
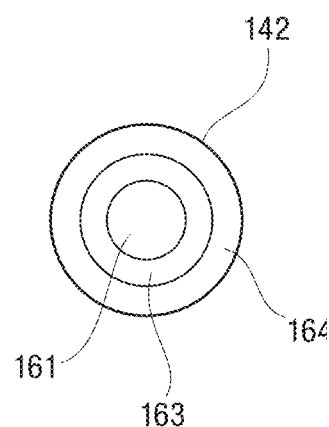
Figure 3C:
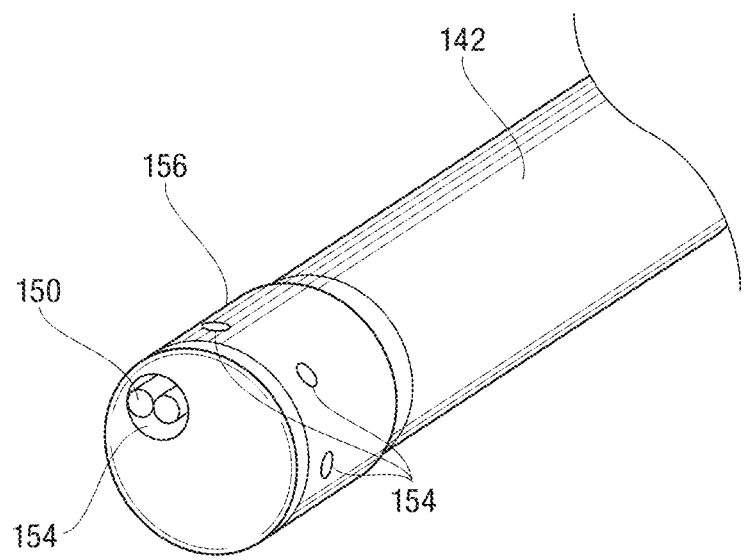

In some embodiments, the distal tip 148 may be configured to act as an electrode for diagnostic purposes, such as for electrogram sensing, for therapeutic purposes, such as for emitting ablation energy, or both. In some embodiments, where ablation energy is used, the distal tip 148 of the catheter 140 could serve as an ablation electrode or ablation element. In some embodiments, the distal end of the catheter can include one or more electrodes. In some embodiments, the distal end of the catheter can include an array of electrodes comprising a plurality of electrodes. In some embodiments, the optical fibers can be associated with the electrodes to determine tissue contact and to decide which electrodes to use during ablation. In some embodiments, an array of electrodes can be disposed on the distal end of the catheter, as shown in FIGS. 3A-3C. In some embodiments, an array of electrodes can be disposed on an expandable member. The expandable member can be in a variety of forms, including a wire basket arrangement shown in FIGS. 5A-5B, a flower arrangement shown in FIG. 5C, and a balloon shown in FIG. 7. A plurality of electrodes are disposed on the expandable members such that at least one of the plurality of electrodes can be in contact with tissue. The system has the ability to determine which of the plurality of electrodes has tissue contact, such that only those electrodes with proper tissue contact are used for tissue ablation. The system also has the ability to determine the type of tissue that each electrode is in contact with, such that only those electrodes with proper tissue contact to the correct type of tissue are used for tissue ablation. For example, if an electrode is determined to be in contact with collagen, that electrode will not be used for ablation.

In some embodiments, the electrodes on the distal tip 148 are coupled to the ablation energy source (external to the catheter), for example by wires or another lumen that can transfer ablation energy, which can be passed through a lumen of the catheter. The distal tip 148 may include a port in communication with the one or more lumens of the catheter. The distal tip 148 can be made of any biocompatible material. In some embodiments, if the distal tip 148 is configured to act as an electrode, the distal tip 148 can be made of metal, including, but not limited to, platinum, platinum-iridium, stainless steel, titanium or similar materials.

In reference to FIGS. 1A and 3A-3C, a distal end of an exemplary ablation catheter is shown that includes an imaging bundle 150 that may be passed from the optical tissue interrogation system 120 of FIG. 1A, through the catheter body 142 such that each optical fiber 152 can pass to each electrode in the array. In some embodiments, each optical fiber is aligned with each electrode. In some embodiments, alternatively or additionally, the imaging bundle includes optical fibers that are not associated with an electrode. At the distal end 146, the catheter 140 may include a distal tip 148, having a side wall 156 and a front wall 158. The front wall 158 may be, for example, flat, conical or dome shaped. The distal end 146 may be provided with one or more optical port 154 associated with the array of electrodes 155 for exchange of light energy between the catheter and tissue. In some embodiments, the optical ports may be made through the electrode, such that the light can pass from the optical fibers through the electrodes. In some embodiments, even with multiple openings 154, the function of the distal tip 148 as an ablation electrode is not compromised. The openings may be disposed on the front wall 156, on the side wall 158 or both. The openings 154 may also be used as irrigation ports. The light is delivered by the fiber 150 to the distal tip 148, where it illuminates the tissue in the proximity of the distal tip 148. This illumination light is either returned or causes the tissue to fluoresce. The light returned by and fluoresced from the tissue may be gathered by the optical fiber 150 within the distal tip 148 and carried back to the optical tissue interrogation system 120. In some embodiments, the same optical fiber or bundle of fibers 150 may be used to both direct light to the illumination chamber of the distal tip to illuminate tissue outside the catheter 140 and to collect light from the tissue.

Figure 4:
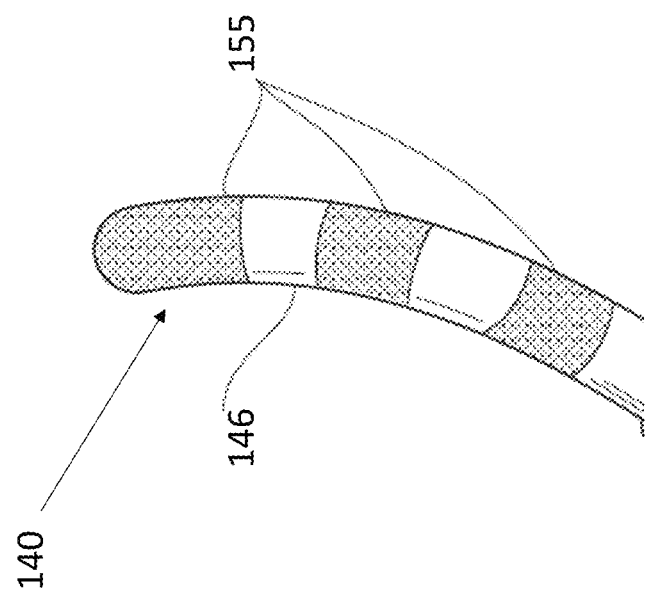
FIG. 4 is an exemplary embodiment of an ablation catheter.

FIG. 4 illustrates an embodiment of an ablation catheter 140 having a distal end 146 with an array of electrodes 155 comprising a plurality of electrodes disposed at the distal end 146.

Figure 5A:
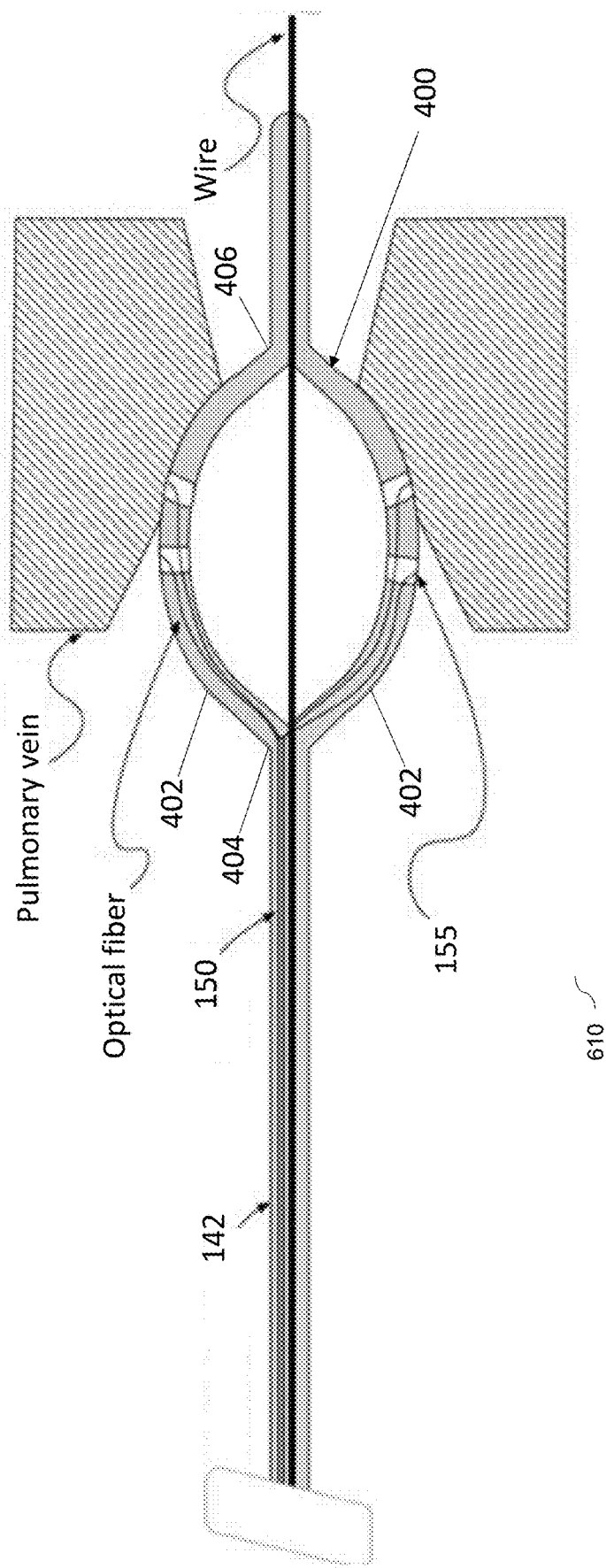
FIG. 5A is an exemplary embodiment of an ablation catheter having an expandable member on a distal end thereof.
Figure 5B:
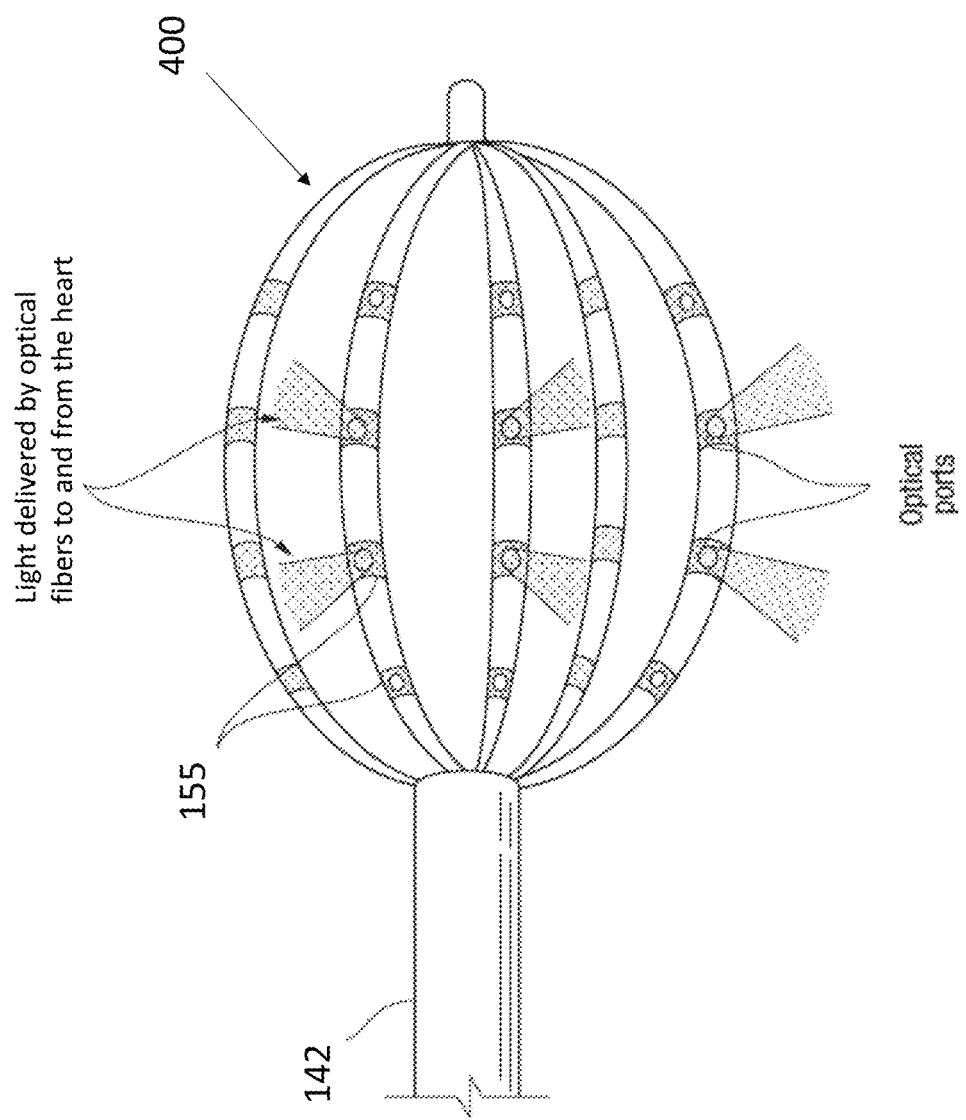
FIG. 5B is a perspective view of the expandable member of FIG. 5A.

As shown in FIGS. 5A and 5B, the array of electrodes 155 can be positioned on an expandable member 400 having a plurality of extensions or splines 402 that are configured to move into an expanded position. While FIG. 5A illustrates two exemplary extensions 402, it will be understood that the expandable member 400 can include any number of extensions 402. In the expanded position, shown in FIG. 5A, each extension 402 can arc such that a proximal end 404 of each extension is coupled to one another and a distal end 406 of each extension is coupled to one another. Each extension 402 of the expandable member 400 can include at least one electrode 155 formed thereon, and each electrode 155 is coupled to at least one optical fiber 152 in the fiber bundle 150. In some embodiments, each electrode 155 is coupled to a single optical fiber 152.

Figure 5C:
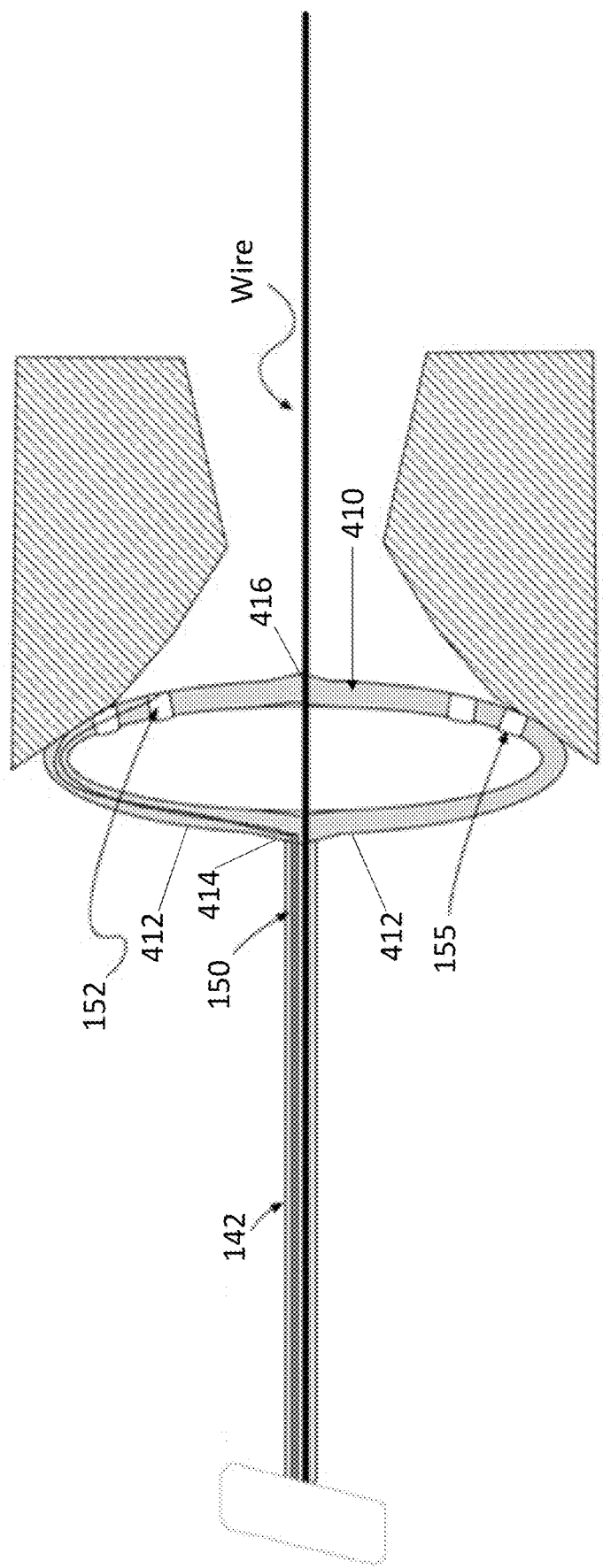
FIG. 5C is an exemplary embodiment of an ablation catheter having an expandable member on a distal end thereof.

Similar to the expandable member shown in FIG. 5A, an expandable member 410 shown in FIG. 5C includes a plurality of extensions or splines 412 such that, when in an expanded position as shown in FIG. 5C, a distance between a proximal end 414 and a distal end 416 of the expandable member 410 is less than the distance shown in FIG. 5A, giving the expandable member 410 an oblong shape along a vertical axis. As the distance between the proximal end and the distal end of the expandable member changes, the position of the distal end of the catheter relative to the tissue changes. For example, as shown in FIG. 5C, the distal end 146 of the catheter 140 can be positioned outside of the pulmonary vein while still allowing the electrodes 155 to make contact with tissue as the electrodes 155 are facing the distal end 146 of the catheter 140.

FIG. 5D illustrates a distal-end view of the catheter 140 and expandable members 400, 410 shown in FIGS. 5A-5C. The shape of the expandable member can be changed to maximize the plurality of electrodes that come in contact with tissue. For example, the more compressed the expandable member (i.e. the more oblong the expandable member is in a vertical direction), the more electrodes will be facing the tissue. This can allow for more electrodes to contact the tissue and for the distal end of the catheter to be positioned adjacent the tissue. For example, in the case of the catheter being positioned adjacent a pulmonary vein, the catheter can be positioned outside the pulmonary vein on the atrial side while still having enough electrodes facing the vein to contact the desired tissue.

Figure 6:
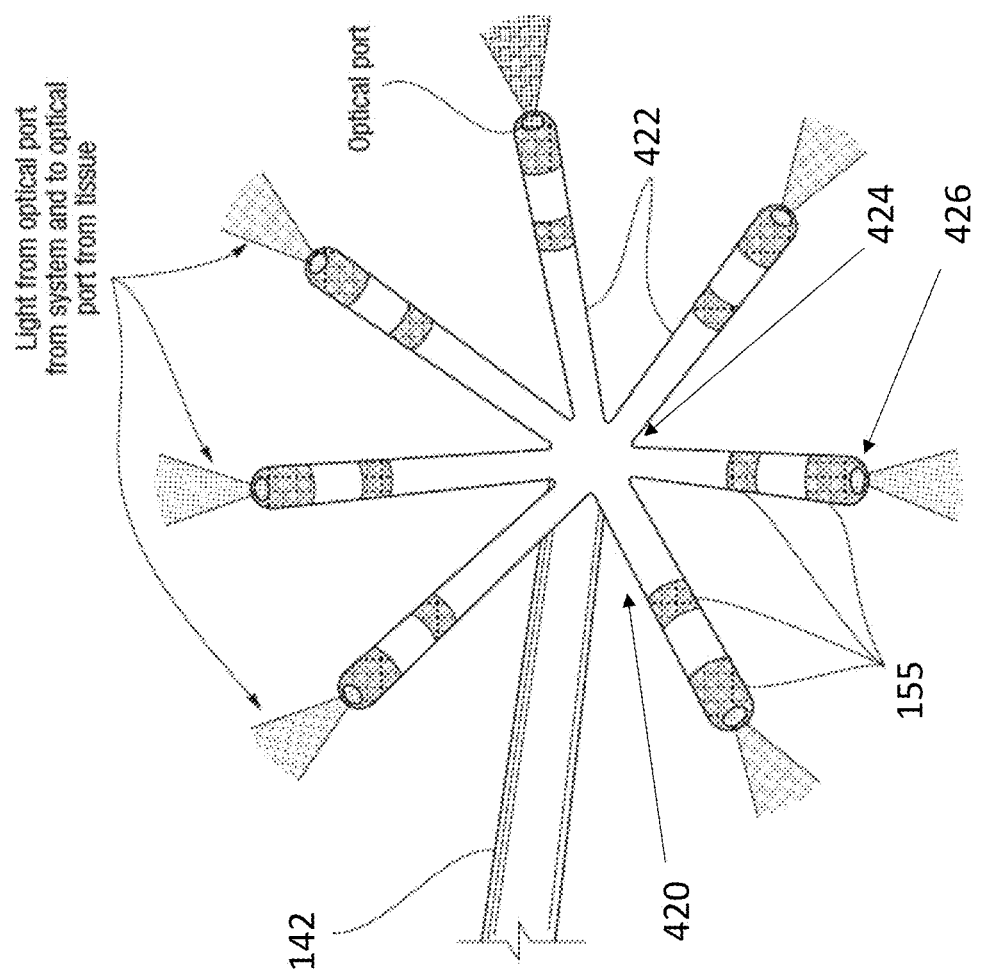
FIG. 6 is an exemplary embodiment of an ablation catheter having an expandable member on a distal end thereof.

FIG. 6 illustrates an embodiment of the expandable member 420 having a plurality of extensions or arms 422 coupled to one another at a proximal end 424. A distal end 426 of each of the plurality of arms 422 extends away from the catheter body 142 such that a plurality of electrodes 155 disposed on the arms 422 can make contact with tissue. It will be understood that the number of arms and size and shape of the arms can vary depending on various factors, including the location of the tissue to be ablated.

FIG. 7 illustrates an embodiment of an expandable member 430 in the form of a balloon having a plurality of electrodes 155 disposed thereon, with each electrode being associated with an optical fiber. The shape of the balloon can be changed to maximize the plurality of electrodes 155 that come in contact with tissue.

In reference to FIGS. 3A-3C, in some embodiments, the catheter may have an optical tissue interrogation lumen 161 through which the optical fiber 150 may be advanced through the catheter body 142. The optical fiber 150 may be advanced through the optical tissue interrogation lumen 161 to illuminate the tissue and receive returned light through the opening 154. As necessary, the optical fiber 150 may be advanced through the opening 154.

In addition to the optical tissue interrogation lumen 161, the catheter 140 may further include an irrigation lumen 163 for passing irrigation fluid from the irrigation system 170 to the openings 154 (irrigation ports) in the distal tip 148 and an ablation lumen 164 for passing ablation energy from the ablation therapy system 110 to the distal tip 148, such as, for example, by passing a wire through the ablation lumen 164 for PFA ablation energy. It should be noted that the lumens of the catheter may be used for multiple purposes and more than one lumen may be used for the same purpose. In addition, while FIG. 3A and FIG. 3B show the lumens being concentric other configurations of lumens may be employed.

As shown in FIG. 3A and FIG. 3B, in some embodiments, a central lumen of the catheter may be utilized as the optical tissue interrogation lumen 161. In some embodiments, as shown in FIG. 3C, the optical tissue interrogation lumen 161 may be off set in relation to the central access of the catheter 140.

In some embodiments, the light may also be directed axially and radially with respect to the catheter. In this manner, the light energy exchange between the catheter and tissue may occur over multiple paths, axially, radially or both with respect to the longitudinal central axis of the catheter. This is useful when the anatomy will not allow the catheter tip to be orthogonal to the target site. It may also be useful when increased illumination is required. In some embodiments, additional optical fibers 150 may be used and may be deflected in the radial direction with respect to the catheter 140 to allow the illumination and returned light to exit and enter along the length of the catheter.

In reference to FIGS. 8A-8D, in some embodiments, an ablation catheter can be used in combination with a sheath that includes the optical fibers such that the optical fibers associated with the sheath can be positioned relative to the catheter to allow the fibers to be associated with the electrodes. In some embodiments, the sheath can be in the form of a deflectable and/or steerable sheath such that a distal end of the sheath and the optical components associated with the sheath can be positioned at a desired location relative to tissue for ablation.

The combination of the sheath and the ablation catheter can have various configurations. In one embodiment shown in FIG. 8A, a sheath 500 includes a plurality of extensions or arms 502 extending from a distal end 504 of the sheath 500. Each arm has a least one optical fiber extending therethrough. The sheath includes an inner lumen extending therethrough such that an ablation catheter can pass through the sheath and extend past the distal end. The ablation catheter can have various configurations, but in FIG. 8A the ablation catheter 140 includes a plurality of extension or arms, with each extension having at least one electrode disposed thereon. The extensions of the distal end of the sheath and the extensions of the ablation catheter are positioned relative to one another to allow a for tissue interrogation by the optical fibers in the arms of the sheath while delivering ablation energy via the electrodes of the ablation catheter. In some embodiments, the extensions of the sheath can be deflectable and/or steerable to allow for proper positioning of the extensions relative to the electrodes and the tissue. In some embodiments, the extensions of the sheath may have more than one optical fiber to optically interrogate the tissue before, during and after ablation energy delivery. In some embodiments, the extensions of the sheath housing the fibers can also have electrodes on them to further assess the tissue. It will be understood that the sheath shown in FIG. 8A can be used with any ablation catheter described herein.

Figure 8B:
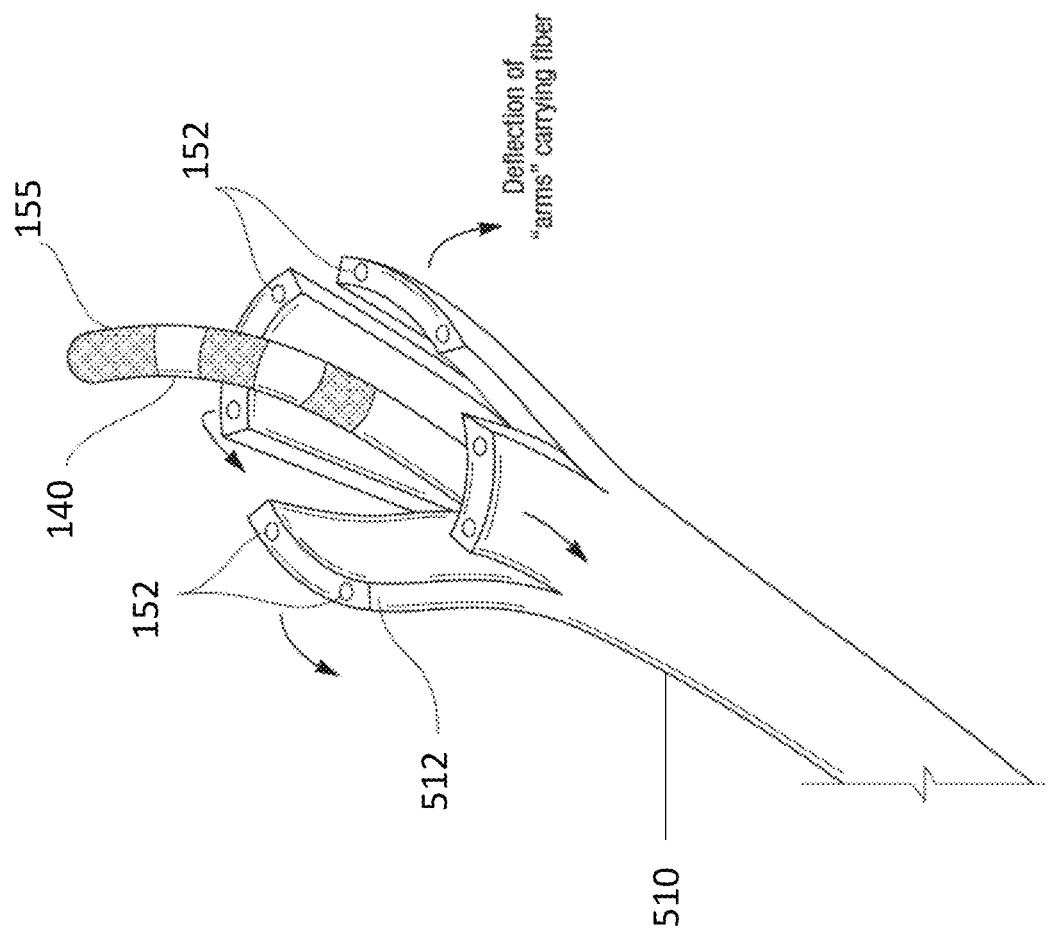

FIG. 8B illustrates an embodiment of a sheath 510 having deflectable and/or steerable extensions or arms 512 extending from a distal end thereof. The distal end of the sheath 510 can be split to form the arms or extensions 512. While the sheath shown in FIG. 8B can be used with any ablation catheter described herein, an ablation catheter 140 can be passed through an inner lumen of the sheath 510 having a plurality of electrodes 155 spaced along its length. In some embodiments, the arms of the sheath may have more than one optical fiber to optically interrogate the tissue before, during and after ablation energy delivery. In some embodiments, the arms of the sheath housing the fibers can also have electrodes on them to further assess the tissue.

Figure 8C:
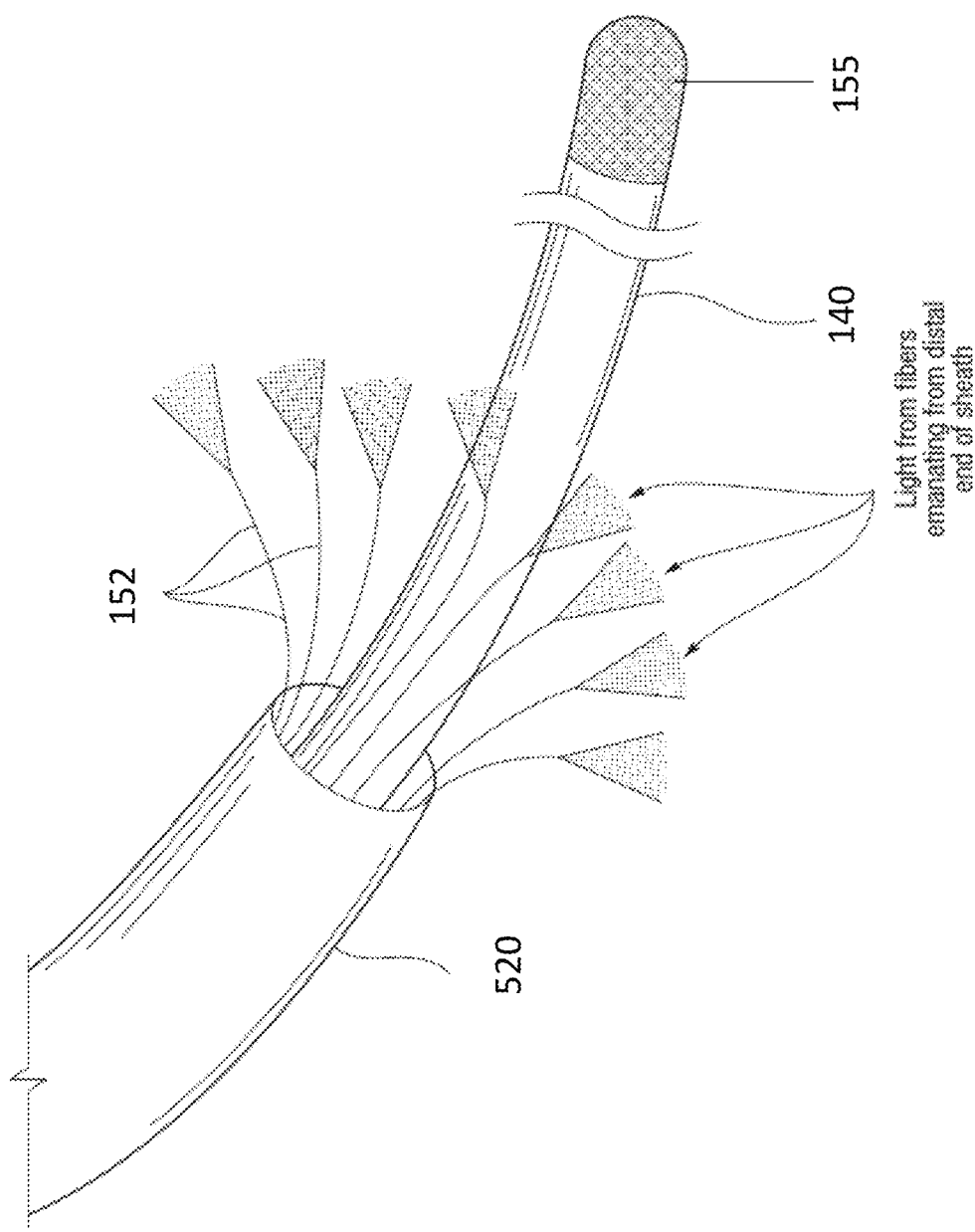

FIG. 8C illustrates an embodiment of a deflectable and/or steerable sheath 520 having a plurality of optical fibers 152 extending from a distal end of the sheath 520. While the sheath shown in FIG. 8C can be used with any ablation catheter described herein, an ablation catheter 140 can be passed through an inner lumen of the sheath 520 having at least one electrode 155 disposed along its length. The optical fibers 152 that extend from the sheath have a length such that they can contact tissue and the electrodes 155 of the ablation catheter.

Figure 8D:
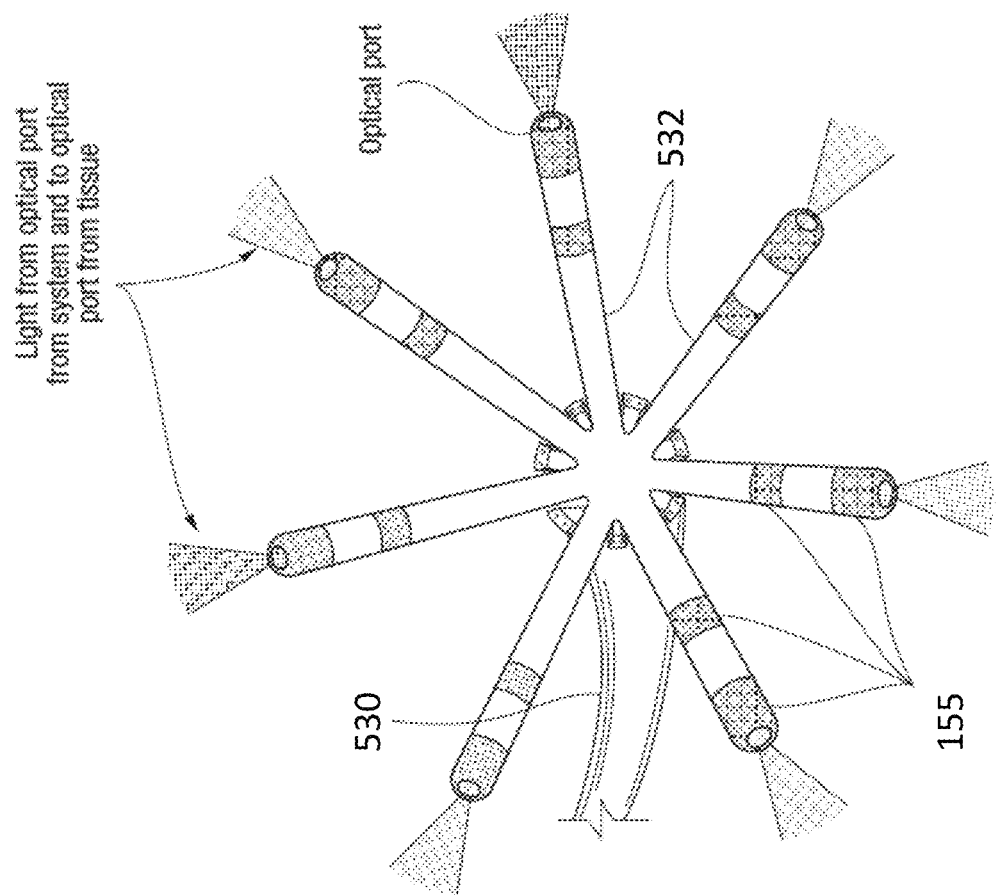

FIG. 8D illustrates an embodiment of a deflectable and/or steerable sheath 530 having a plurality of optical fibers extending from a distal end of the sheath. The ablation catheter that extend through the sheath can have various configurations, including any of the ablation catheters described herein, but in FIG. 8D the ablation catheter includes a plurality of extension or arms 532, with each extension having at least one electrode 155 disposed thereon. The extensions of the distal end of the sheath and the extensions of the ablation catheter are positioned relative to one another to allow a connection between the optical fibers in the extensions of the sheath and the electrodes on the extensions of the ablation catheter.

FIG. 8D also illustrates an embodiment of a deflectable and/or steerable catheter having a plurality of electrodes at the distal end of the catheter. The various flexible ablation arms of the ablation catheter can have various configurations, but in FIG. 8D the ablation catheter includes a plurality of extension or arms, with each extension having at least one electrode disposed thereon. The extensions of the ablation catheter are positioned relative to one another to optimally deliver energy to the tissue in a circumferential pattern, while, when combined with a sheath of the present disclosure, optically interrogating the tissue using the fibers which deliver light to the tissue via each optical port.

Figure 9:
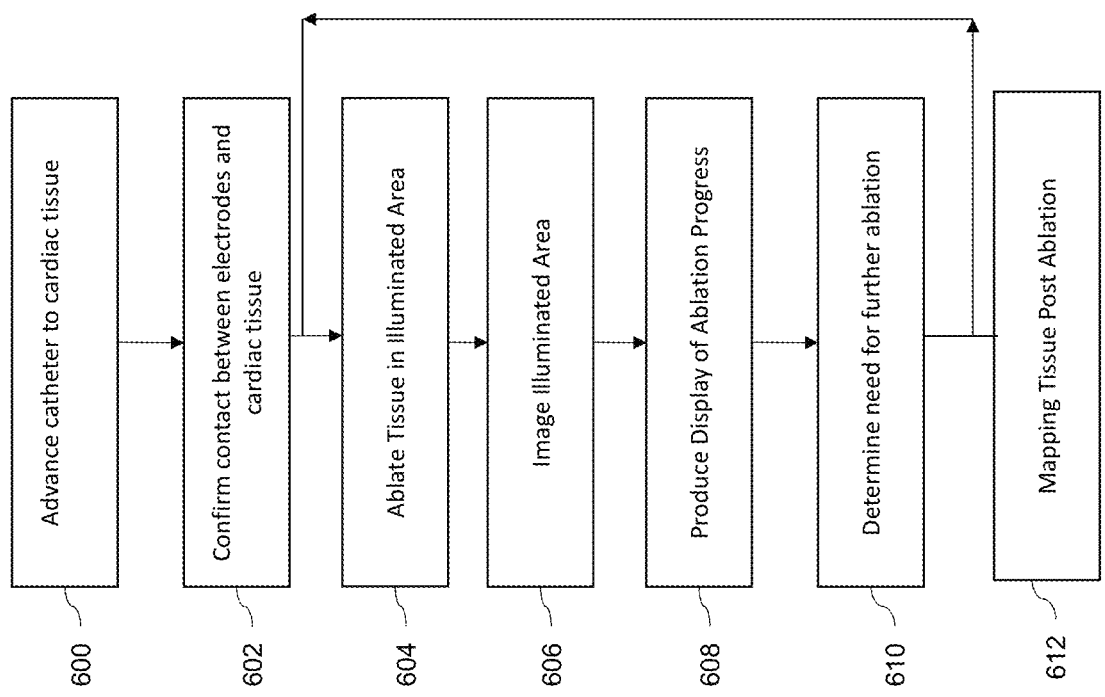
FIG. 9 illustrates a flowchart of a method for interrogating, monitoring, and ablating tissue.

FIG. 9 is a flow chart of a method of using a system of the present disclosure.

In reference to FIG. 9, operation of the system 100 of the present disclosure is illustrated. Initially, the catheter 140 is inserted into the area of heart tissue to be ablated, such as the pulmonary vein/left atrial junction or another area of the heart (step 600). As shown for example, in FIGS. 5A and 5C, in some embodiments, the catheter 140 may be advanced through the pulmonary vein and pressed against the heart tissue. Blood may be removed from the visual field, for example, by irrigation.

Figure 10:
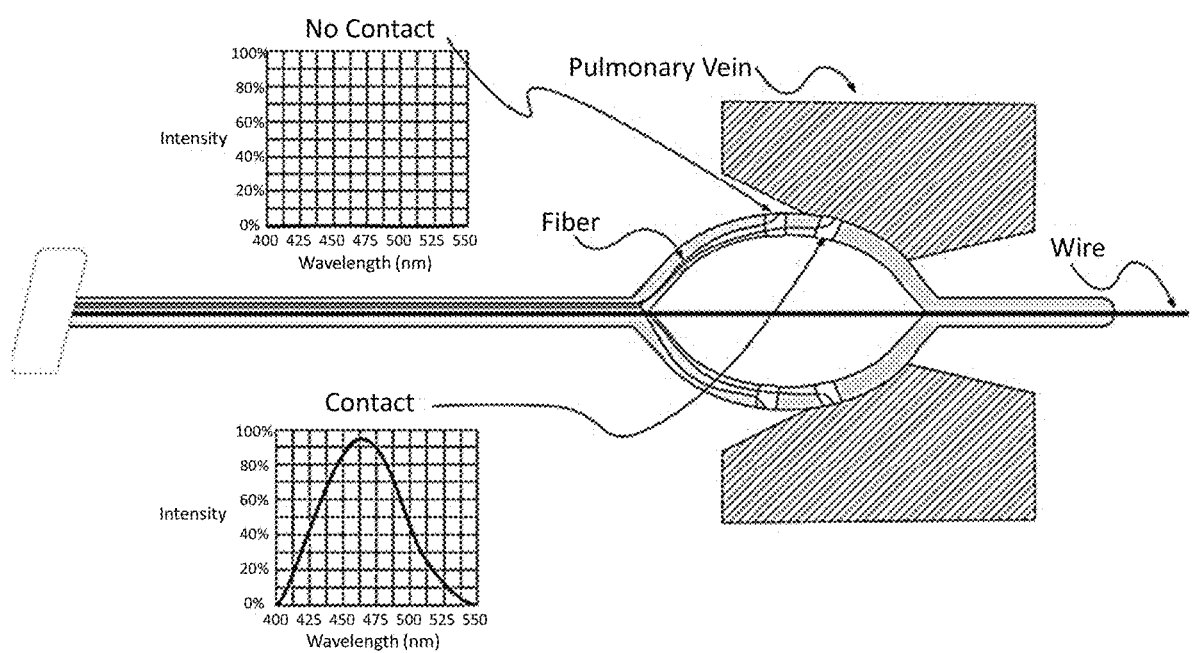
FIG. 10 illustrates an exemplary embodiment of an ablation catheter with electrodes that are in contact with tissue and electrodes that are not in contact with tissue and their corresponding response signals.
Figure 11:
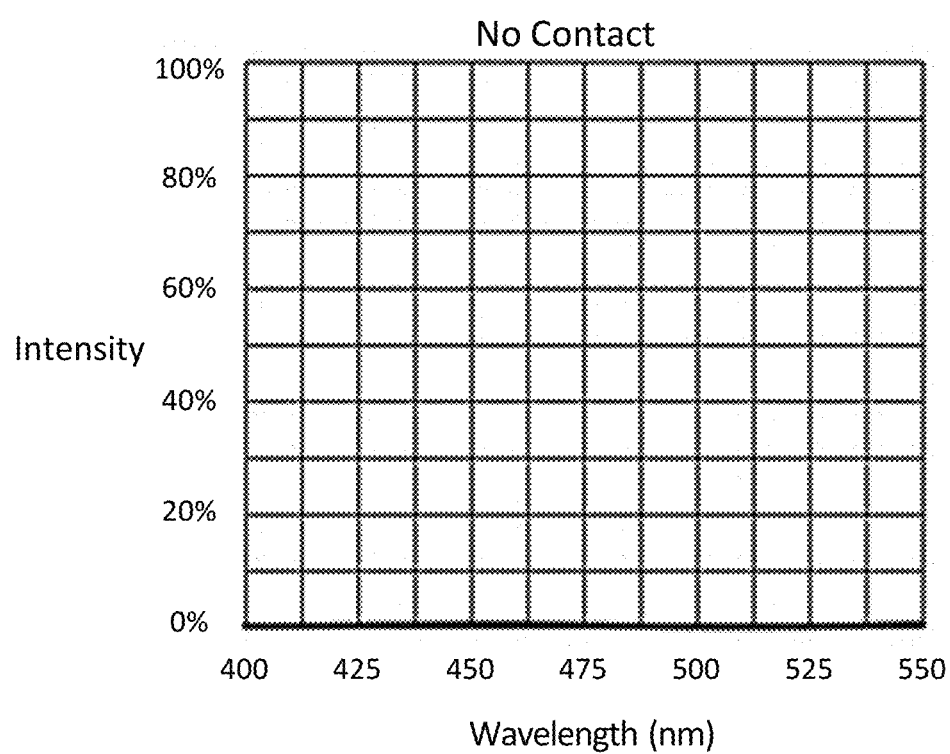
FIG. 11 illustrates an exemplary graph of response light intensity when an electrode of an ablation catheter is not in contact with tissue.

Next, in step 602, the contact between the electrodes with tissue can be confirmed. In some embodiments, where the fibers are associated with the electrodes, the tissue can be eliminated through the fibers and the returned light is interrogated to confirm the contact between the individual electrodes and the tissue. For example, as shown in FIG. 10 and FIG. 11, there will be no NADH fluorescence detected for the electrodes that are not in contact with the cardiac tissue.

Figure 12:
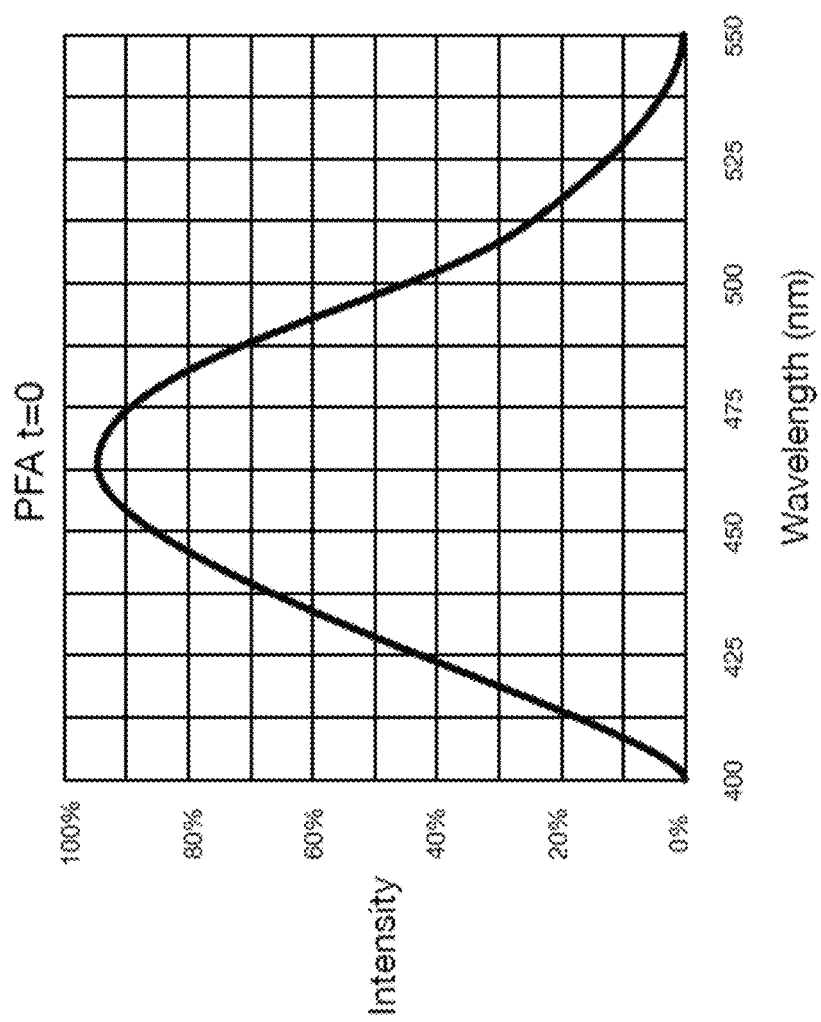
FIGS. 12, 13, and 14 show optical intensity pre- and post-PFA.
Figure 13:
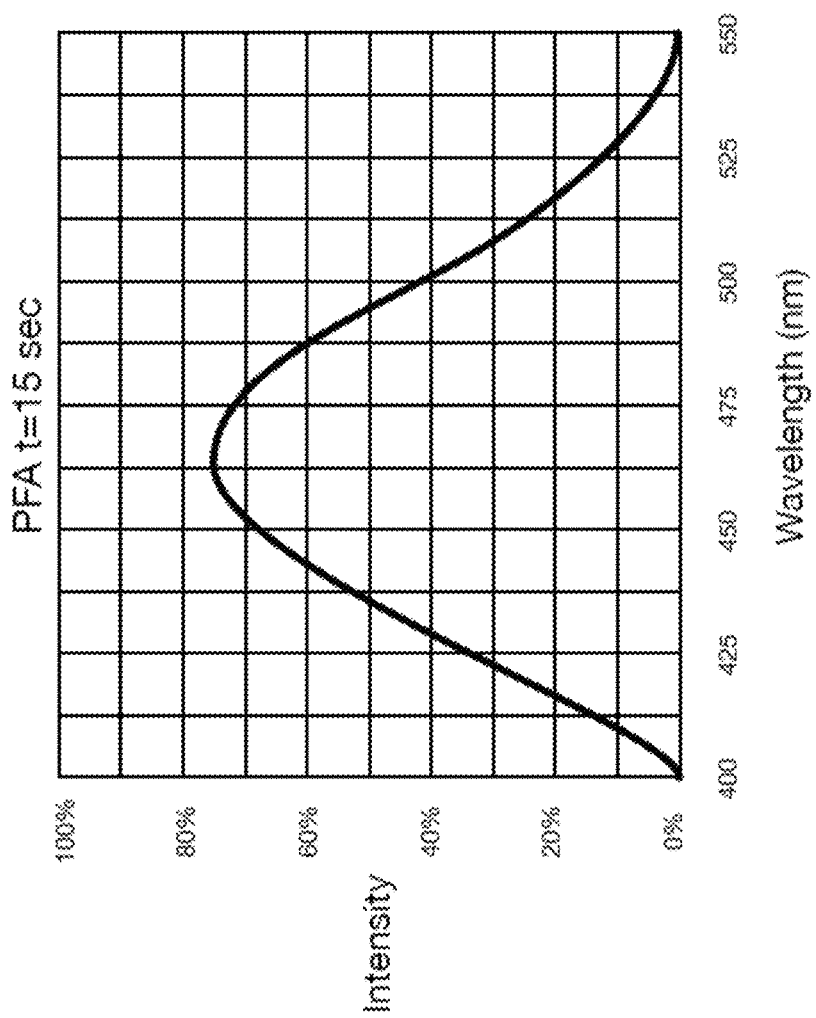
Figure 14:
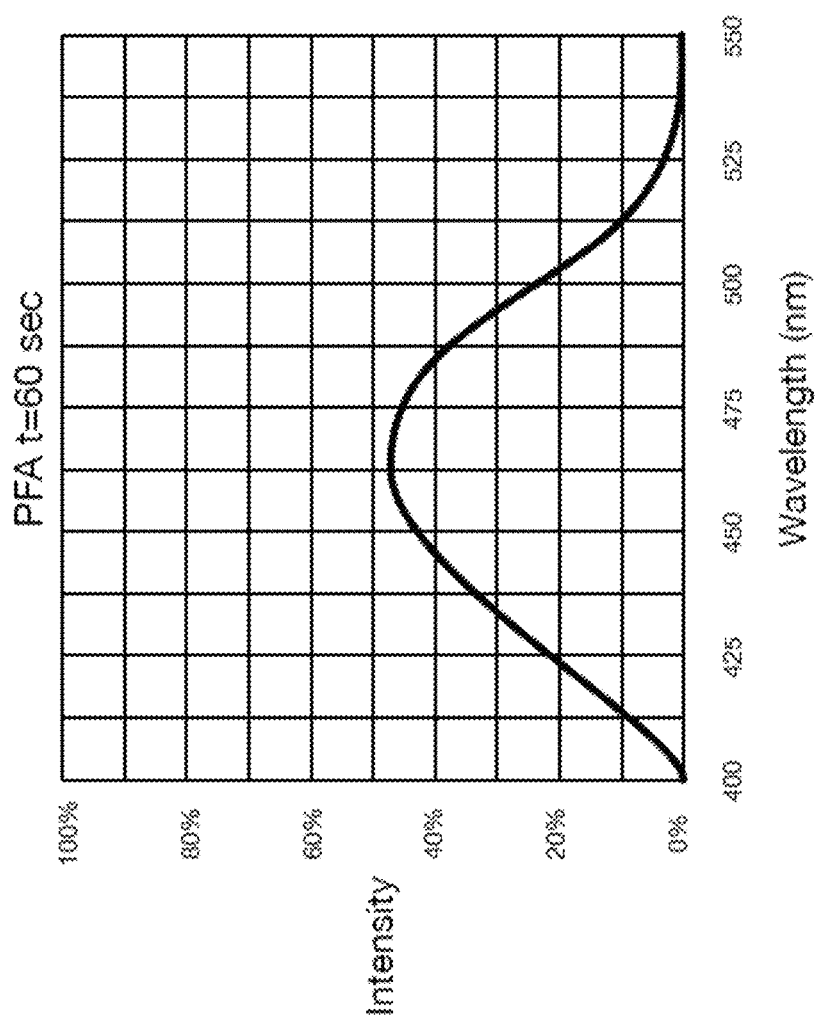
Figure 15:
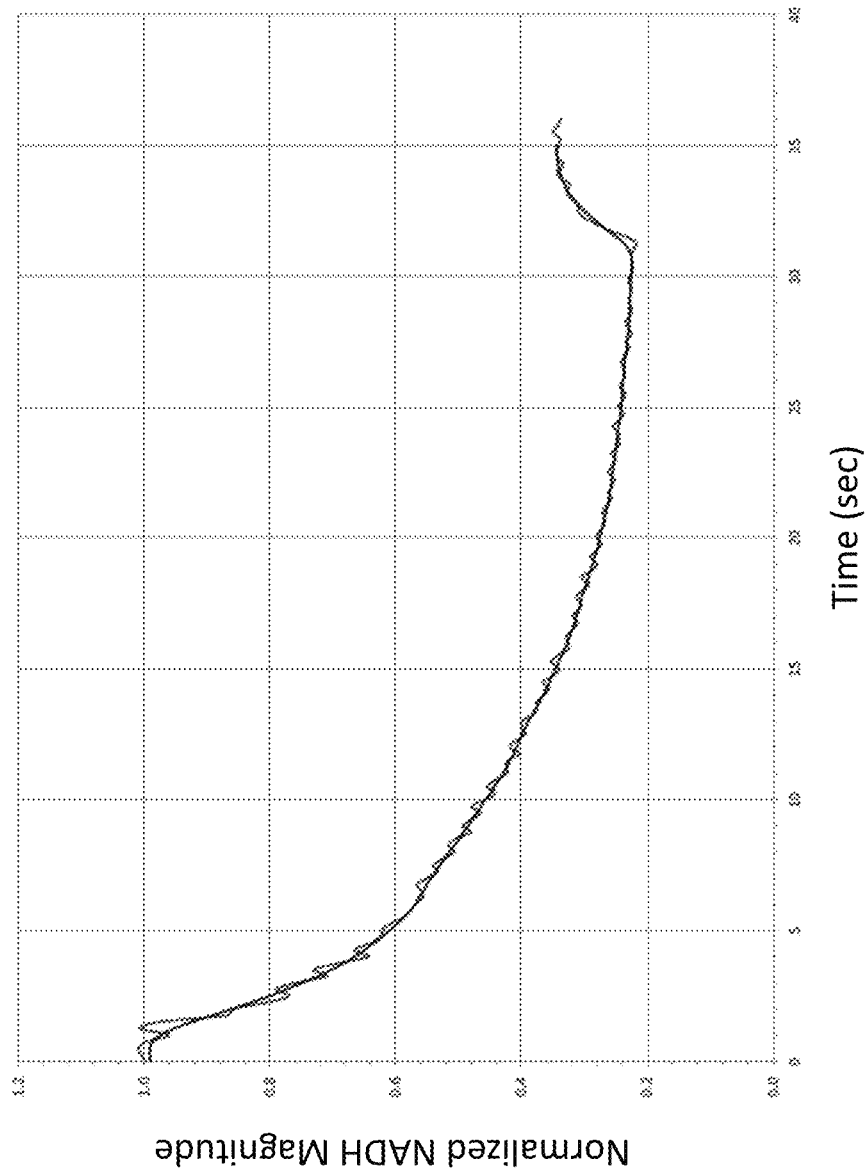
FIG. 15 illustrates an exemplary graph of NADH fluorescence over time during ablation.
Figure 16B:
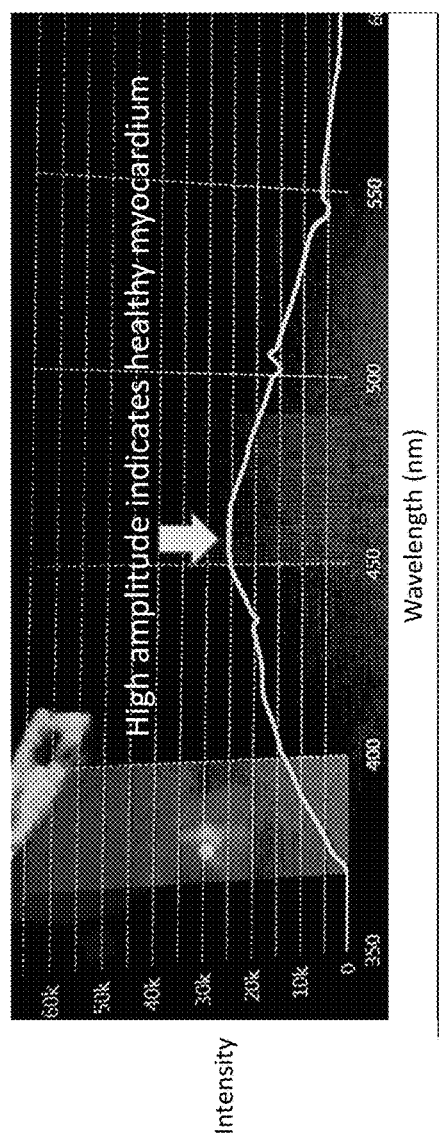
FIGS. 16A, 16B, 16C, and 16D show optical mapping of healthy tissue and ablation lesions.
Figure 16A:
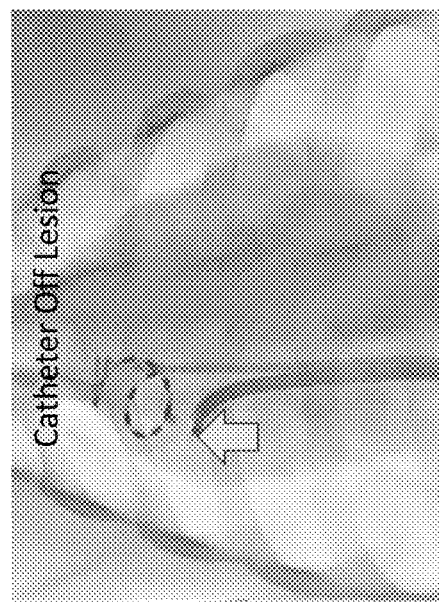
Figure 16D:
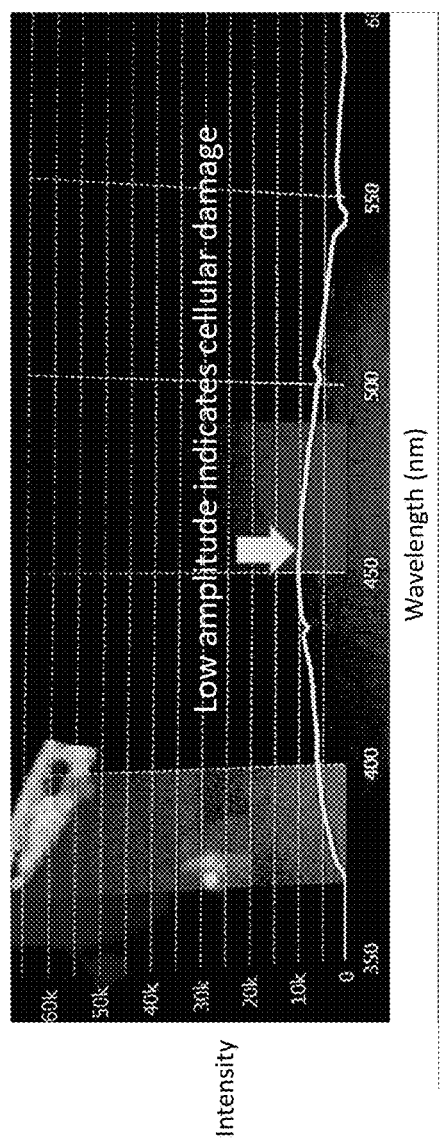
Figure 16C:
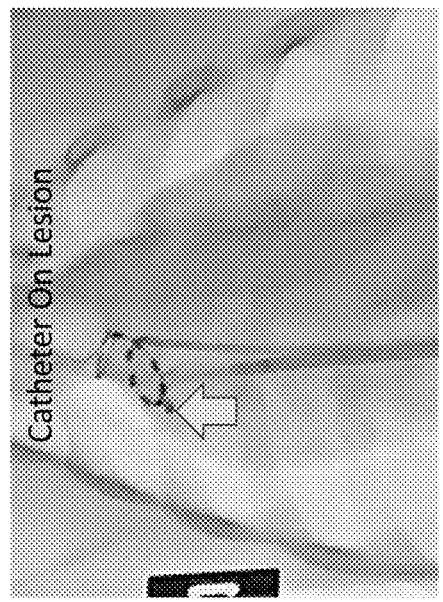

In step 604, the electrodes that are in contact with the tissue can be activated to ablate the tissue. The tissue is illuminated, in step 608, using the fibers, and the light returned from the tissue is detected and analyzed in order to show the progress of the ablation in real time in step 608. As shown in FIGS. 12-14, the intensity of the NADH fluorescence decrease as the ablation progresses. This effect is due to the reduction of metabolic activity and hence reduction of the NADH fluorescence as the cells are ablated. This drop may be used as an indication when to stop ablation. For example, in reference to FIG. 15, the user may be presented with a graph or another graphical representation of the NADH fluorescence showing the change in the NADH fluorescence to aid the user in monitoring the progress of the ablation, as represented by step 610. At this step, the user is also enabled to determine whether to continue or stop the ablation. In some embodiments, the ablation may continue until a desired change in the magnitude of the NADH fluorescence is achieved, at which point the ablation may be stopped, either manually or autonomously by the system. For example, in some embodiments, the ablation may be stopped upon reduction in the NADH signal by 80% or more. Once the ablation is stopped, the system of the present embodiment can be used to map the tissue, in step 612, to identify the areas of damaged cells (such as by ablation) or the areas of healthy myocardium that can be ablated, as shown in FIGS. 16A-16D. The system can store such pre-ablation and post-ablation signals and optical information for the purpose of documenting the extent of energy delivery to the tissue in a given location. In some embodiments, such data in real time or post-ablation from signals stored can be analyzed via an algorithm to assess or predict the probability of the creation of a durable lesion In some embodiments, the spectral signature may be collected and analyzed to determine tissue composition. For example, the spectral pattern of collagenous tissue is different than the one seen on healthy myocardium. When illuminated in this case with a 355 nm UV light source, the peak of the spectrum shifts to the left (from about 470 nm to about 445 nm) when imaging over collagenous tissue to shorter wavelengths due to increased effect of collagen fluorescence. This may be used by the user to identify the area that is being treated as being mostly myocardium or being covered by collagen, which is harder to ablate. In particular, a digital representation of collagen florescence is indicative of fibrous formations in the tissue of the fibrotic burden of the tissue. There are potential benefits associated with the information content of the returned spectrum to the physician during the ablation procedure. The technique of coupling light into tissue from a catheter or specifically an ablation electrode at the distal tip of a catheter can be used to determine and assess the quality of contact that the catheter or the electrode has with the tissue. Knowing more information about the type of tissue being ablated, or whether or not the presence, and possibly the degree, of collagen in the tissue to be ablated ahead of ablation energy deployment may also affect the ablation strategy and technique used by the physician for optimal creation of that lesion. For example, in the presence of collagen, a physician may elect one ablation energy source over another and the power or duration or temperature limits may be adjusted higher to achieve a deeper lesion given the collagenous nature of the tissue being ablated. The collagenous tissue can have a different fibrotic burden than muscle tissue, and thus require a different ablation strategy.

The following examples are put forth to provide those of ordinary skill in the art with a complete disclosure and description of how to make and use the assay, screening, and therapeutic methods of the present disclosure, and are not intended to limit the scope of what the inventors regard as their invention.

EXAMPLES

A series of 3 anesthetized pigs underwent PFA ablation in the right atrium. An 8-electrode circular catheter was placed high in the right atrium, near the superior vena cava, to simulate pulmonary vein isolation as part of an AF ablation procedure. The optical catheter was placed adjacent to the circular catheter between stimulation electrode pairs. A bolus of adenosine was administered to create a window of asystole to avoid stimulation on the T-wave. Bipolar PFA was delivered immediately post drug infusion and the optical signature from the catheter was recorded and displayed in real time. Electrograms were recorded and the mapping of the lesion was performed with the optical catheter at the following time intervals post PFA delivery: 0 min, 15 seconds, 30 seconds, 1 minute (60 seconds), 15 min, 1 hour, and 3 hours. Necropsy and histology followed the procedure.

For this example, separate PFA catheter and an optical tissue interrogation catheter were used. For optical tissue interrogation, the following parameters were used: Excitation wavelength 355 nm; Collagen response 375 to 400 nm; Myocardial response 450 to 475 nm and Peak tracking vs. time at 465 nm FIGS. 12-14 are representative of optical intensity pre- and post-PFA. FIG. 10 shows optical intensity response to PFA.

The optical signal is distinctly higher in intensity during the PFA pulse train. The optical signal showed an immediate significant decrease and a slow but steady decay over the mapping interval. Electrogram reduction accompanied PFA application and also showed a marked reduction over the mapping interval. The optical signal amplitudes were markedly lower when on the lesion compared to healthy non-ablated myocardium as predicted.

These results indicate that optical mapping detects immediate tissue changes during PFA at these energy levels and hence can be a viable method of evaluating lesion formation during and after PFA energy application. The optical signal indicates that cell damage occurs immediately at these energy levels and continues to progress slowly in lesions made by PFA energy compared to those made by RF energy. The findings also suggest that optical mapping can identify acute lesions made with PFA energy in real time implying that optical mapping could be used as a PFA gap detector. Findings also suggest that the optical tissue interrogation or mapping can be used to predict the durability or non-durability of PFA lesions.

Other Embodiments

From the foregoing description, it will be apparent that variations and modifications may be made to the embodiments of the present disclosure to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A system for optical tissue interrogation comprising:
a catheter having an expandable member at a distal end thereof, the expandable member including a plurality of extensions being coupled together at a proximal end and a distal end such that, when the expandable member is expanded, the plurality of extensions are configured to arc;
each of the plurality of extensions supporting a plurality of electrodes being configured to deliver ablation energy to tissue; and
one or more optical fibers extending through the catheter to deliver light from a light source to the tissue and to deliver optical information comprising nicotinamide adenine dinucleotide hydrogen (NADH) fluorescence from the tissue to a sensor, wherein each electrode of the plurality of electrodes is associated with at least one of the one or more optical fibers
wherein each of the plurality of electrodes comprises an optical port and the one or more optical fibers are aligned with the optical port to enable the light to pass through the optical port.

2. The system of claim 1, wherein the light source has at least one wavelength sufficient to excite mitochondrial nicotinamide adenine dinucleotide hydrogen (NADH) in the tissue.

3. The system of claim 1, wherein the sensor is configured to receive light having at least one wavelength to detect the NADH fluorescence from the tissue.

4. The system of claim 1, wherein the ablation energy is pulsed field ablation energy.

5. The system of claim 4, wherein the sensor is configured to receive light having at least one wavelength between about 375 nm and about 650 nm.

6. The system of claim 1, wherein the ablation energy is selected from a group consisting of electroporation energy, radiofrequency energy, microwave energy, electrical energy, electromagnetic energy, cryoenergy, laser energy, ultrasound energy, acoustic energy, chemical energy, and thermal energy.

7. The system of claim 1, wherein the light for illuminating the tissue has at least one wavelength between about 300 nm and about 400 nm.

8. The system of claim 1 further comprising a processor in communication with the sensor and configured to generate a digital representation of the NADH fluorescence to distinguish between ablated tissue and non-ablated tissue.

9. The system of claim 1 further comprising a processor in communication with the sensor and programmed to:
obtain the NADH fluorescence from the sensor during ablation of the tissue;
generate a digital representation of the NADH fluorescence for monitoring a progression of the ablation of the tissue, wherein a decrease in the NADH fluorescence is indicative of the progression of the ablation of the tissue to enable a user to determine a need for further ablation, and
while the tissue is being ablated, monitoring the decrease in the NADH fluorescence and updating the digital representation to show the decrease in the NADH fluorescence throughout the ablation of the tissue.

10. The system of claim 9, the optical information is used to predict durability of a lesion in the tissue created by ablating the tissue.

11. The system of claim 1, wherein the light and the sensor are configured to receive light having at least one wavelength to detect collagen fluorescence from the tissue.

12. The system of claim 11 further comprising a processor in communication with the sensor and configured to generate a digital representation of the collagen fluorescence to assess a fibrotic burden of the tissue.

13. A system for optical tissue interrogation comprising:
a catheter having a plurality of electrodes disposed in an array at a distal end of the catheter, the plurality of electrodes being configured to deliver ablation energy to tissue; and
a sheath configured to slidably receive the catheter therethrough, the sheath comprising one or more optical fibers extending through the sheath to deliver light from a light source to the tissue and to deliver nicotinamide adenine dinucleotide hydrogen (NADH) fluorescence from the tissue to a sensor, wherein the sheath is configured to associate each electrode of the plurality of electrodes with at least one of the one or more optical fibers, the sheath including a plurality of deflectable extensions at the distal end thereof, each deflectable extension of the plurality of deflectable extensions having at least one optical fiber extending therethrough, and wherein one or more electrodes of the plurality of electrodes are disposed on the distal end of the plurality of deflectable extensions,
wherein each of the plurality of electrodes comprises an optical port and the one or more optical fibers are aligned with the optical port to enable the light to pass through the optical port.

14. The system of claim 13, wherein the ablation energy is selected from a group consisting of pulsed field ablation energy, electroporation energy, radiofrequency energy, microwave energy, electrical energy, electromagnetic energy, cryoenergy, laser energy, ultrasound energy, acoustic energy, chemical energy, and thermal energy.

15. The system of claim 13, wherein the light for illuminating the tissue has at least one wavelength between about 300 nm and about 400 nm and the sensor is configured to receive light having at least one wavelength between about 375 nm and about 650 nm.

16. The system of claim 13, wherein each of the plurality of electrodes comprises an optical port and the one or more optical fibers are aligned with the optical port to enable the light to pass through the optical port.

17. The system of claim 13 further comprising a processor in communication with the sensor is configured to generate a digital representation of the NADH fluorescence to distinguish between ablated tissue and non-ablated tissue.

18. The system of claim 13, wherein the sheath splits to form the plurality of deflectable extensions.

19. A method for optical tissue interrogation comprising:
receiving an NADH fluorescence from a tissue, wherein the tissue is illuminated through one or more optical fibers associated with a plurality of electrodes configured to deliver ablation energy to the tissue, the plurality of electrodes being supported on a plurality of extensions of an expandable member, the plurality of extensions of the expandable member being coupled together at a proximal end and a distal end such that, when the expandable member is expanded, the plurality of extensions are configured to arc, and each of the plurality of electrodes comprises an optical port and the one or more optical fibers are aligned with the optical port to enable light to pass through the optical port;
indicating which electrodes of the plurality of electrodes are in contact with the tissue, wherein the ablation energy is delivered only from the electrodes of the plurality of electrodes that are in contact with the tissue; and
generating a digital representation of the NADH fluorescence for monitoring a progression of the ablation of the tissue, wherein a decrease in the NADH fluorescence from the illuminated tissue is indicative of the progression of the ablation of the tissue to enable a user to determine a need for further ablation.

20. The method of claim 19 further comprising determining, while the tissue is being ablated, a decrease in the NADH fluorescence and updating the digital representation to show the decrease in the NADH fluorescence throughout the ablation of the tissue.

21. The method of claim 19, wherein the ablation energy is selected from a group consisting of pulsed field ablation energy, electroporation energy, radiofrequency energy, microwave energy, electrical energy, electromagnetic energy, cryoenergy, laser energy, ultrasound energy, acoustic energy, chemical energy, and thermal energy.

22. The method of claim 19, wherein the tissue is illuminated with light having at least one wavelength between about 300 nm and about 400 nm and light returned from the tissue has at least one wavelength between about 375 nm and about 650 nm.

* * * * *